(12) United States Patent
Wang et al.

(10) Patent No.: US 10,821,104 B2
(45) Date of Patent: Nov. 3, 2020

(54) FIVE-MEMBERED HETEROCYCLIC AMIDES WNT PATHWAY INHIBITOR

(71) Applicant: SUZHOU SINOVENT PHARMACEUTICALS CO., LTD., Jiangsu (CN)

(72) Inventors: Yonghui Wang, Zhejiang (CN); Yan Zhu, Zhejiang (CN); Juan Zhou, Zhejiang (CN); Yujun Gao, Zhejiang (CN); Shiqun Wang, Zhejiang (CN); Dong Wang, Zhejiang (CN); Wandeng Liu, Zhejiang (CN); Ximing Shen, Zhejiang (CN); Binbin Hong, Zhejiang (CN); Tao Liu, Zhejiang (CN); Yaodong Wu, Zhejiang (CN); Chunqi Li, Zhejiang (CN)

(73) Assignee: Suzhou Sinovent Pharmaceuticals Co., Ltd., Jiangsu (CN)

( * ) Notice: Subject to any disclaimer, the term of this patent is extended or adjusted under 35 U.S.C. 154(b) by 0 days.

(21) Appl. No.: 16/060,146

(22) PCT Filed: Dec. 7, 2016

(86) PCT No.: PCT/CN2016/108964
§ 371 (c)(1),
(2) Date: Jun. 7, 2018

(87) PCT Pub. No.: WO2017/097216
PCT Pub. Date: Jun. 15, 2017

(65) Prior Publication Data
US 2018/0271846 A1    Sep. 27, 2018

(30) Foreign Application Priority Data

Dec. 7, 2015  (CN) .......................... 2015 1 0887508

(51) Int. Cl.
| | | |
|---|---|---|
| *C07D 401/14* | (2006.01) |
| *C07D 413/14* | (2006.01) |
| *C07D 417/14* | (2006.01) |
| *A61K 31/444* | (2006.01) |
| *A61K 31/497* | (2006.01) |
| *C07D 413/12* | (2006.01) |
| *C07D 417/12* | (2006.01) |
| *C07D 401/12* | (2006.01) |
| *A61P 35/00* | (2006.01) |
| *A61K 31/4427* | (2006.01) |
| *A61K 31/506* | (2006.01) |

(52) U.S. Cl.
CPC ........ *A61K 31/444* (2013.01); *A61K 31/4427* (2013.01); *A61K 31/497* (2013.01); *A61K 31/506* (2013.01); *A61P 35/00* (2018.01); *C07D 401/12* (2013.01); *C07D 401/14* (2013.01); *C07D 413/12* (2013.01); *C07D 413/14* (2013.01); *C07D 417/12* (2013.01); *C07D 417/14* (2013.01)

(58) Field of Classification Search
CPC ... C07D 401/14; C07D 413/14; C07D 417/14
See application file for complete search history.

(56) References Cited

FOREIGN PATENT DOCUMENTS

| | | |
|---|---|---|
| CN | 102596910 A | 7/2012 |
| CN | 103717593 A | 4/2018 |
| WO | WO-2009131957 A2 | 10/2009 |
| WO | WO-2010033626 A1 | 3/2010 |
| WO | WO-2014210159 A1 | 12/2014 |

*Primary Examiner* — Brian E McDowell
(74) *Attorney, Agent, or Firm* — Muncy, Geissler, Olds & Lowe, P.C.

(57) ABSTRACT

A five-membered heterocyclic amide WNT pathway inhibitor having the following general structural formula:

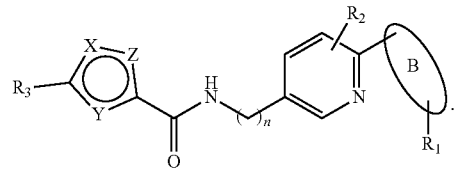

The five-membered heterocyclic amide WNT pathway inhibitor has a remarkable anti-tumor activity based on a target-based rational drug design, and can be used for the development of a new generation of Wnt pathway inhibitors, and has a great clinical application value and considerable market potential.

9 Claims, 2 Drawing Sheets

FIVE-MEMBERED HETEROCYCLIC AMIDES WNT PATHWAY INHIBITOR

TECHNICAL FIELD

The present invention relates to a five-membered heterocyclic amide Wnt pathway inhibitor, which belongs to a compound that regulates the activity of a Wnt signaling pathway, and provides a method for preparing such a compound, and the use of such a compound in the preparation of drugs antagonizing the Wnt signaling pathway.

BACKGROUND

The Wnt signaling pathway plays an important role in the life process such as multicellular organism axis differentiation, tissue organogenesis, and tumorigenesis. Proteins encoded by Wnt genes are a type of secreted glycoprotein consisting of 19 members, that activates multiple intracellular signaling pathways such as typical Wnt/β-catenin pathway, planar polarity pathway, and Wnt/$Ca^{2+}$ pathway by binding to Frizzled (Fzd) family protein and low-density lipoprotein receptor-related protein (LDL receptor related protein, LRP) receptors, and regulates multiple cell functions including proliferation, differentiation, death, migration, polarization, etc. (Nusse Roel, Varmus Harold E. (1992). Wnt genes. Cell, 69(7), 1073-1087).

According to study reports, it was found that the dysregulation of the activation of β-catenin-TCF/LCF transcription complexes in typical Wnt/β-catenin signaling pathway is involved in the pathogenesis of neurological diseases, inflammatory fibrotic diseases, metabolic diseases, and various types of cancers (Kahn, M. (2014). Can we safely target the Wnt pathway?. Nature reviews. Nat. Rev. Drug. Discovery, 13(7), 513-532). In the field of cancer research, the evidence for Wnt signaling involved in early carcinogenesis was obtained from oncogene Intl activation in mouse breast cancer caused by virus insertion; and the carcinogenesis of nearly 10% of the patients suffering from colorectal, head and neck, lung, ovarian and melanoma cancers are associated with functional mutation induction in Wnt signaling regulating elements R-spondin family and RNF43/ZNRF3 (B Madan, Z Ke, N Harmston, et al. (2015). Wnt addiction of genetically defined cancers reversed by PORCN inhibition. Oncogene, 1-11). However, there are currently no clinically available small molecule targeted drug specific to Wnt signaling pathway for patients, and the non-selective cytotoxic agents and combination therapies thereof adversely affect patients' quality of life due to adverse reactions such as gastrointestinal reactions and bone marrow hematopoietic suppression. At present, drug candidates entering the clinical trial stage are still in the stage of clinical phase VII for verification of their safety and conceptual drug efficacy. For example, LGK974 (ClinicalTrials.gov Identifier: NCT01351103) and ETC-1922159 (ClinicalTrials.gov Identifier: NCT02521844) designed for the upstream target PORCN of the Wnt signaling pathway; and PRI-724 (ClinicalTrials.gov Identifier: NCT02413853) designed for the downstream target CBP/β-catenin of the Wnt signaling pathway. In view of this, it is of important clinical value and social significance to continue to develop drugs regulating the Wnt signaling pathway, with a clear mechanism of action and significant efficacy.

SUMMARY OF THE INVENTION

The object of the present invention is to provide a five-membered heterocyclic amide Wnt pathway inhibitor with a novel structure, wherein a series of compounds having an anti-tumor activity are synthesized through the substitution and modification of groups and screened.

In order to achieve the above-mentioned object, the present invention adopts the following technical solution:

A five-membered heterocyclic amide Wnt pathway inhibitor having the following general structural formula, or a pharmaceutically acceptable salt thereof:

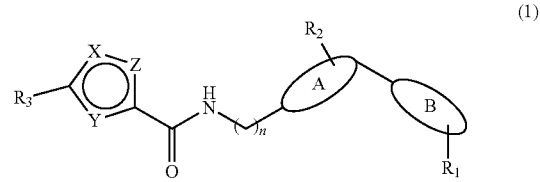

(1)

wherein ring A and ring B are each independently selected from an aromatic ring or an aromatic heterocyclic ring containing 1-2 N atom(s) or O atom(s); X, Y and Z are each independently selected from one of a group consisting of $CR_4$, $NR_5$, S atom and O atom, and the S atom and O atom are not present simultaneously; n is selected from any integer within the range of 1 to 2; $R_1$ and $R_2$ are each independently selected from one or more of a group consisting of hydrogen, halogen, $C_{1-6}$ alkyl, $C_{3-6}$ cycloalkyl, $C_{2-6}$ alkenyl, $C_{2-6}$ alkynyl, halogenated $C_{1-6}$ alkyl, $C_{1-6}$ alkoxy, halogenated $C_{1-6}$ alkoxy, hydroxy, amino, acyl, sulfo, aryl, and heterocyclyl; $R_3$ is one or more of a substituted or unsubstituted aryl or heterocyclyl group, wherein the substituents on the aryl and heterocyclyl groups are selected from one or more of a group consisting of halogen, $C_{1-6}$ alkyl, halogenated $C_{1-6}$ alkyl, $C_{1-6}$ alkoxy, halogenated $C_{1-6}$ alkoxy, hydroxyl, cyano, amino, acyl, sulfo, and heterocyclyl; $R_4$ and $R_5$ are each independently selected from one of a group consisting of hydrogen, $C_{1-6}$ alkyl, halogenated $C_{1-6}$ alkyl, $C_{1-6}$ alkoxy, halogenated $C_{1-6}$ alkoxy and $C_{3-6}$ cycloalkyl; and the heterocyclyl is a 3-12 membered heterocyclic ring containing one or more atom(s) selected from a group consisting of N, O and S atoms.

Preferably, having the following general structural formula or pharmaceutically acceptable salts thereof:

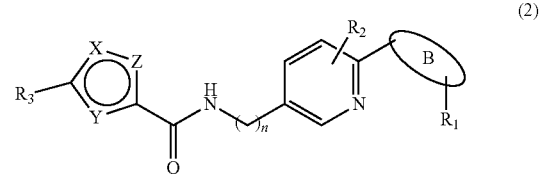

(2)

wherein ring B is selected from an aromatic ring or an aromatic heterocyclic ring containing 1-2 N atom(s) or O atom(s); X, Y and Z are each independently selected from one of a group consisting of $CR_4$, $NR_5$, S atom and O atom, and the S atom and O atom are not present simultaneously; n is selected from any integer within the range of 1 to 2; $R_1$ and $R_2$ are each independently selected from one or more of a group consisting of hydrogen, halogen, $C_{1-6}$ alkyl, $C_{3-6}$ cycloalkyl, halogenated $C_{1-6}$ alkyl, $C_{1-6}$ alkoxy, halogenated $C_{1-6}$ alkoxy, hydroxy, amino, acyl, aryl, and heterocyclyl; $R_3$ is one or more of a substituted or unsubstituted aryl or heterocyclyl group, wherein the substituents on the aryl and heterocyclyl groups are selected from one or more of a group consisting of halogen, $C_{1-6}$ alkyl, halogenated $C_{1-6}$ alkyl, $C_{1-6}$ alkoxy, halogenated $C_{1-6}$ alkoxy, hydroxyl, cyano, amino, acyl, sulfo, and heterocyclyl; $R_4$ and $R_5$ are each independently selected from one of a group consisting of hydrogen, $C_{1-6}$ alkyl, halogenated $C_{1-6}$ alkyl, $C_{1-6}$ alkoxy, halogenated $C_{1-6}$ alkoxy and $C_{3-6}$ cycloalkyl; and the heterocyclyl is a 3-6 membered heterocyclic ring containing one or more atom(s) selected from a group consisting of N, O and S atoms.

More preferably, in the general structural formula (2),

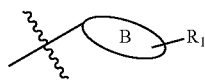

is selected from one of a group consisting of

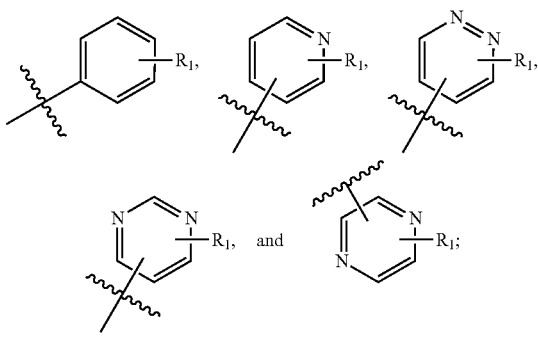

X, Y and Z are each independently selected from one of a group consisting of $CR_4$, $NR_5$, S atom and O atom, and the S atom and O atom are not present simultaneously; n is selected from any integer within the range of 1 to 2; $R_1$ and $R_2$ is selected from one of a group consisting of hydrogen, halogen, $C_{1-6}$ alkyl, $C_{1-6}$ alkoxy, halogenated $C_{1-6}$ alkyl, halogenated $C_{1-6}$ alkoxy, amido, $C_{1-6}$ alkylamido, and heterocyclyl; $R_3$ is selected from one of a group consisting of

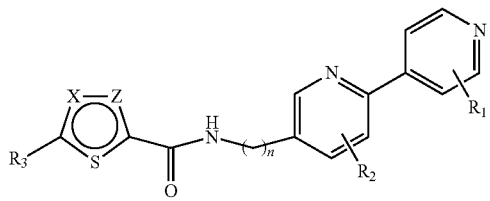

$R_4$ and $R_5$ are each independently selected from one of a group consisting of hydrogen, $C_{1-6}$ alkyl, halogenated $C_{1-6}$ alkyl, $C_{1-6}$ alkoxy, and halogenated $C_{1-6}$ alkoxy group; $R_6$ is selected from one of a group consisting of hydrogen, halogen, $C_{1-6}$ alkyl, halogenated $C_{1-6}$ alkyl, $C_{1-6}$ alkoxy, halogenated $C_{1-6}$ alkoxy, and amido group; and the heterocyclyl is a 3-6 membered heterocyclic ring containing one or more atom(s) selected from a group consisting of N and O atoms.

Preferably, having the following general structural formula or pharmaceutically acceptable salts thereof:

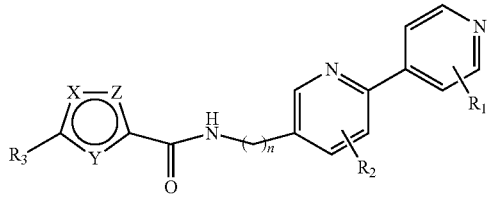

(3)

wherein X, Y and Z are each independently selected from one of a group consisting of $CR_4$, $NR_5$, S atom and O atom, and the S atom and O atom are not present simultaneously; n is selected from 1 or 2; $R_1$ and $R_2$ is selected from one of a group consisting of hydrogen, halogen, $C_{1-6}$ alkyl, $C_{1-6}$ alkoxy, halogenated $C_{1-6}$ alkyl, halogenated $C_{1-6}$ alkoxy, amido, $C_{1-6}$ alkylamido, and heterocyclyl; $R_3$ is selected from one of a group consisting of

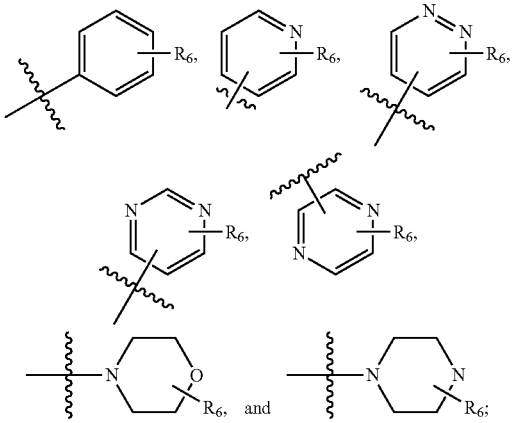

$R_4$ and $R_5$ are each independently selected from one of a group consisting of hydrogen, $C_{1-6}$ alkyl, halogenated $C_{1-6}$ alkyl, $C_{1-6}$ alkoxy, and halogenated $C_{1-6}$ alkoxy; $R_6$ is selected from one of a group consisting of hydrogen, halogen, $C_{1-6}$ alkyl, halogenated $C_{1-6}$ alkyl, $C_{1-6}$ alkoxy, halogenated $C_{1-6}$ alkoxy, and amido group; and the heterocyclyl is a 3-6 membered heterocyclic ring containing one or more atom(s) selected from a group consisting of N and O atoms. More preferably, having the following general structural formula and pharmaceutically acceptable salts thereof:

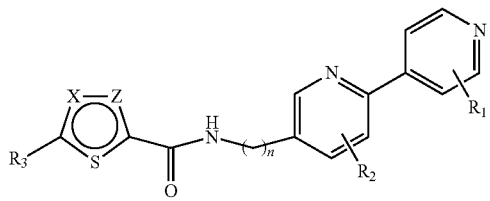

(4)

wherein X and Z are $CR_4$ at the same time; or X and Z are $NR_5$ at the same time; or any of X and Z is $CR_4$, and the other is $NR_5$; n is selected from 1 or 2; $R_1$ and $R_2$ is selected from one of a group consisting of hydrogen, halogen, $C_{1-6}$ alkyl, $C_{1-6}$ alkoxy, halogenated $C_{1-6}$ alkyl, halogenated $C_{1-6}$ alkoxy, amido, $C_{1-6}$ alkylamido, and heterocyclyl; $R_3$ is selected from one of a group consisting of

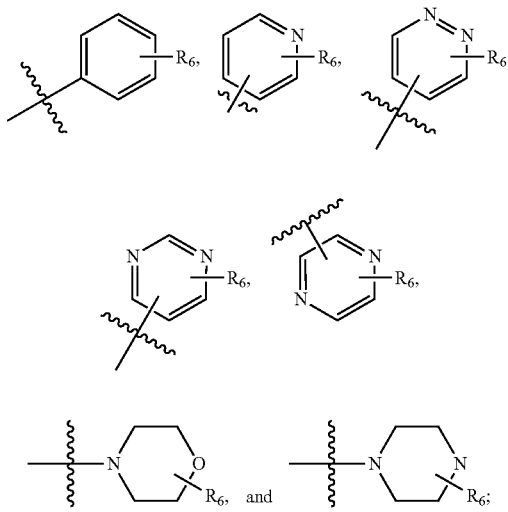

$R_6$ is selected from one of a group consisting of hydrogen, halogen, $C_{1-6}$ alkyl, halogenated $C_{1-6}$ alkyl, $C_{1-6}$ alkoxy, halogenated $C_{1-6}$ alkoxy, and amido group; and the heterocyclyl is a 3-6 membered heterocyclic ring containing one or more atom(s) selected from a group consisting of N and O atoms.

Preferably, having the following general structural formula or pharmaceutically acceptable salts thereof:

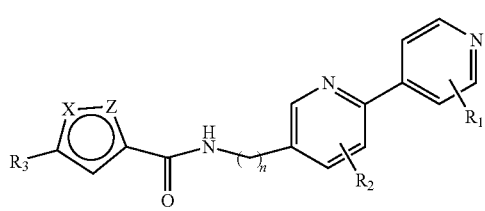

(5)

wherein X and Z are $CR_4$ at the same time; or X and Z are $NR_5$ at the same time; or any of X and Z is $CR_4$, and the other is $NR_5$; or any of X and Z is O atom, and the other is $NR_5$; or any of X and Z is O atom, and the other is $CR_4$; n is selected from 1 or 2; $R_1$ and $R_2$ is selected from one of a group consisting of hydrogen, halogen, $C_{1-6}$ alkyl, $C_{1-6}$ alkoxy, halogenated $C_{1-6}$ alkyl, halogenated $C_{1-6}$ alkoxy, amido, $C_{1-6}$ alkylamido, and heterocyclyl; $R_3$ is selected from one of a group consisting of

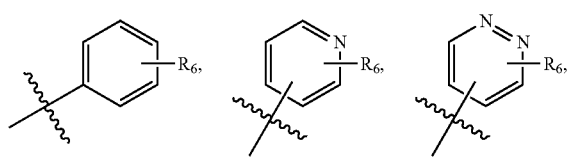

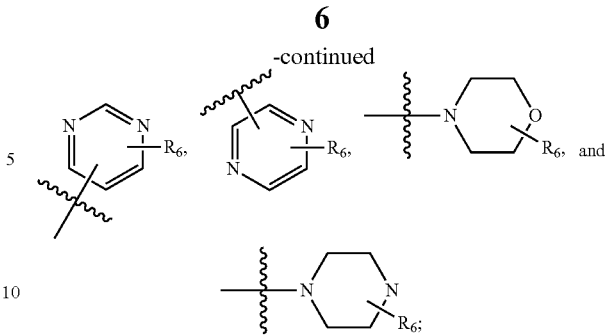

$R_6$ is selected from one of a group consisting of hydrogen, halogen, $C_{1-6}$ alkyl, halogenated $C_{1-6}$ alkyl, $C_{1-6}$ alkoxy, halogenated $C_{1-6}$ alkoxy, and amido group; and the heterocyclyl is a 3-6 membered heterocyclic ring containing one or more atom(s) selected from a group consisting of N and O atoms.

Preferably, the aryl group is a phenyl, naphthyl or anthryl group; the heterocyclyl group is a morpholinyl, piperidyl, pyridyl, pyrimidinyl, pyranyl, thienyl, furyl, pyrrolyl, pyrazolyl, imidazolyl or thiazolyl group; and the halogen is selected from one of a group consisting of fluorine, chlorine, bromine and iodine.

A five-membered heterocyclic amide Wnt pathway inhibitor, selected from the following characteristic compounds with identification numbers of REX-P-1 to REX-P-56:

REX-P-1:
N-((2',3-dimethyl-[2,4'-bipyridin]-5-yl)methyl)-1-methyl-3-phenyl-1H-pyrazole-5-carboxamide;

REX-P-2:
N-((2',3-dimethyl-[2,4'-bipyridin]-5-yl)methyl)-5-phenyl-1H-pyrazole-3-carboxamide REX-P-3:
N-((2',3-dimethyl-[2,4'-bipyridin]-5-yl)methyl)-2-phenylthiazole-5-carboxamide;

REX-P-4:
N-((2',3-dimethyl-[2,4'-bipyridin]-5-yl)methyl)-5-phenylthiazole-2-carboxamide;

REX-P-5:
N-((2',3-dimethyl-[2,4'-bipyridin]-5-yl)methyl)-2-phenylthiazole-4-carboxamide;

REX-P-6:
N-((2',3-dimethyl-[2,4'-bipyridin]-5-yl)methyl)-4-phenylthiazole-2-carboxamide;

REX-P-7:
N-((2',3-dimethyl-[2,4'-bipyridin]-5-yl)methyl)-5-phenylisoxazole-3-carboxamide;

REX-P-8:
N-((2',3-dimethyl-[2,4'-bipyridin]-5-yl)methyl)-5-phenyl-1,3,4-thiadiazole-2-carboxamide;

REX-P-9:
N-((2',3-dimethyl-[2,4'-bipyridin]-5-yl)methyl)-1-methyl-5-phenyl-1H-pyrazole-3-carboxamide;

REX-P-10:
N-((2',3-dimethyl-[2,4'-bipyridin]-5-yl)methyl)-4-methyl-5-phenylthiazole-2-carboxamide;

REX-P-11:
5-(2-chlorophenyl)-N-((2',3-dimethyl-[2,4'-bipyridin]-5-yl)methyl)thiazole-2-carboxamide;

REX-P-12:
5-(3-chlorophenyl)-N-((2',3-dimethyl-[2,4'-bipyridin]-5-yl)methyl)thiazole-2-carboxamide;

REX-P-13:
5-(4-chlorophenyl)-N-((2',3-dimethyl-[2,4'-bipyridin]-5-yl)methyl)thiazole-2-carboxamide;
REX-P-14:
N-((2',3-dimethyl-[2,4'-bipyridin]-5-yl)methyl)-5-(pyridin-2-yl)thiazole-2-carboxamide;
REX-P-15:
N-((2',3-dimethyl-[2,4'-bipyridin]-5-yl)methyl)-5-(pyrazin-2-yl)thiazole-2-carboxamide;
REX-P-16:
N-((2',3-dimethyl-[2,4'-bipyridin]-5-yl)methyl)-5-(pyridin-2-yl)-1H-pyrazole-3-carboxamide;
REX-P-17:
N-((2',3-dimethyl-[2,4'-bipyridin]-5-yl)methyl)-5-(3-fluoropyridin-2-yl)-1H-pyrazole-3-carboxamide;
REX-P-18:
N-((2',3-dimethyl-[2,4'-bipyridin]-5-yl)methyl)-5-(5-fluoropyridin-3-yl)-1H-pyrazole-3-carboxamide;
REX-P-19:
N-((2',3-dimethyl-[2,4'-bipyridin]-5-yl)methyl)-5-(6-methylpyridin-2-yl)-1H-pyrazole-3-carboxamide;
REX-P-20:
N-((2',3-dimethyl-[2,4'-bipyridin]-5-yl)methyl)-5-(pyrimidin-2-yl)-1H-pyrazole-3-carboxamide;
REX-P-21:
N-((2',3-dimethyl-[2,4'-bipyridin]-5-yl)methyl)-5-(pyrazin-2-yl)-1H-pyrazole-3-carboxamide;
REX-P-22:
N-((2',3-dimethyl-[2,4'-bipyridin]-5-yl)methyl)-5-(pyrazin-2-yl)-1H-pyrazole-3-carboxamide;
REX-P-23:
N-((2',3-dimethyl-[2,4'-bipyridin]-5-yl)methyl)-2-(pyridin-2-yl)thiazole-5-carboxamide;
REX-P-24:
N-((2',3-dimethyl-[2,4'-bipyridin]-5-yl)methyl)-2-(3-fluoropyridin-2-yl)thiazole-5-carboxamide;
REX-P-25:
N-((2',3-dimethyl-[2,4'-bipyridin]-5-yl)methyl)-2-(5-fluoropyridin-3-yl)thiazole-5-carboxamide;
REX-P-26:
N-((2',3-dimethyl-[2,4'-bipyridin]-5-yl)methyl)-2-(6-methylpyridin-2-yl)thiazole-5-carboxamide;
REX-P-27:
N-((2',3-dimethyl-[2,4'-bipyridin]-5-yl)methyl)-2-(pyrimidin-2-yl)thiazole-5-carboxamide;
REX-P-28:
N-((2',3-dimethyl-[2,4'-bipyridin]-5-yl)methyl)-2-(pyrazin-2-yl)thiazole-5-carboxamide;
REX-P-29:
N-((2',3-dimethyl-[2,4'-bipyridin]-5-yl)methyl)-5-(pyridin-2-yl)isoxazole-3-carboxamide;
REX-P-30:
N-((2',3-dimethyl-[2,4'-bipyridin]-5-yl)methyl)-5-(3-fluoropyridin-2-yl)isoxazole-3-carboxamide;
REX-P-31:
N-((2',3-dimethyl-[2,4'-bipyridin]-5-yl)methyl)-5-(5-fluoropyridin-3-yl)isoxazole-3-carboxamide;
REX-P-32:
N-((2',3-dimethyl-[2,4'-bipyridin]-5-yl)methyl)-5-(6-methylpyridin-2-yl)isoxazole-3-carboxamide;
REX-P-33:
N-((2',3-dimethyl-[2,4'-bipyridin]-5-yl)methyl)-5-(pyrimidin-2-yl)isoxazole-3-carboxamide;
REX-P-34:
N-((2',3-dimethyl-[2,4'-bipyridin]-5-yl)methyl)-5-(pyrazin-2-yl)isoxazole-3-carboxamide;
REX-P-35:
5-(4-acetylpiperazin-1-yl)-N-((2',3-dimethyl-[2,4'-bipyridin]-5-yl)methyl)isoxazole-3-carboxamide;
REX-P-36:
N-((2',3-dimethyl-[2,4'-bipyridin]-5-yl)methyl)-5-(pyridin-3-yl)thiazole-2-carboxamide;
REX-P-37:
N-((2',3-dimethyl-[2,4'-bipyridin]-5-yl)methyl)-5-(3-fluoropyridin-2-yl)thiazole-2-carboxamide;
REX-P-38:
N-((2',3-dimethyl-[2,4'-bipyridin]-5-yl)methyl)-5-(5-fluoropyridin-3-yl)thiazole-2-carboxamide;
REX-P-39:
N-((2',3-dimethyl-[2,4'-bipyridin]-5-yl)methyl)-5-(6-methylpyridin-2-yl)thiazole-2-carboxamide;
REX-P-40:
N-((2',3-dimethyl-[2,4'-bipyridin]-5-yl)methyl)-5-(pyrimidin-2-yl)thiazole-2-carboxamide;
REX-P-41:
N-((2',3-dimethyl-[2,4'-bipyridin]-5-yl)methyl)-5-(pyrimidin-5-yl)thiazole-2-carboxamide;
REX-P-42:
5-(4-acetylpiperazin-1-yl)-N-((2',3-dimethyl-[2,4'-bipyridin]-5-yl)methyl)-1,3,4-thiadiazole-2-carboxamide;
REX-P-43:
5-(4-acetylpiperazin-1-yl)-N-((2',3-dimethyl-[2,4'-bipyridin]-5-yl)methyl)thiazole-2-carboxamide;
REX-P-44:
2-(4-acetylpiperazin-1-yl)-N-((2',3-dimethyl-[2,4'-bipyridin]-5-yl)methyl)thiazole-5-carboxamide;
REX-P-45:
5-(3-chlorophenyl)-N-((2',3-dimethyl-[2,4'-bipyridin]-5-yl)methyl)-1,3,4-thiadiazole-2-carboxamide;
REX-P-46:
N-((2',3-dimethyl-[2,4'-bipyridin]-5-yl)methyl)-5-(3-fluorophenyl)-1,3,4-thiadiazole-2-carboxamide;
REX-P-47:
N-((2',3-dimethyl-[2,4'-bipyridin]-5-yl)methyl)-5-(pyridin-2-yl)-1,3,4-thiadiazole-2-carboxamide;
REX-P-48:
N-((2',3-dimethyl-[2,4'-bipyridin]-5-yl)methyl)-5-(3-fluoropyridin-2-yl)-1,3,4-thiadiazole-2-carboxamide;
REX-P-49:
N-((2',3-dimethyl-[2,4'-bipyridin]-5-yl)methyl)-5-(5-fluoropyridin-3-yl)-1,3,4-thiadiazole-2-carboxamide;
REX-P-50:
N-((2',3-dimethyl-[2,4'-bipyridin]-5-yl)methyl)-5-(6-methylpyridin-2-yl)-1,3,4-thiadiazole-2-carboxamide;
REX-P-51:
N-((2',3-dimethyl-[2,4'-bipyridin]-5-yl)methyl)-5-(pyrimidin-2-yl)-1,3,4-thiadiazole-2-carboxamide;
REX-P-52:
N-((2',3-dimethyl-[2,4'-bipyridin]-5-yl)methyl)-5-(pyrazin-2-yl)-1,3,4-thiadiazole-2-carboxamide;
REX-P-53:
N-((2',3-dimethyl-[2,4'-bipyridin]-5-yl)methyl)-5-(5-methylpyridin-3-yl)-1,3,4-thiadiazole-2-carboxamide;
REX-P-54:
N-((2',3-dimethyl-[2,4'-bipyridin]-5-yl)methyl)-5-(2-methylpyridin-3-yl)-1,3,4-thiadiazole-2-carboxamide;
REX-P-55:
N-((2',3-dimethyl-[2,4'-bipyridin]-5-yl)methyl)-5-(4-methylpyridin-3-yl)-1,3,4-thiadiazole-2-carboxamide; and
REX-P-56:
N-((2',3-dimethyl-[2,4'-bipyridin]-5-yl)methyl)-5-(3-methylpyridin-2-yl)-1,3,4-thiadiazole-2-carboxamide.

The above-mentioned characteristic compounds with identification numbers of REX-P-1 to REX-P-56, have the following specific structures:
REX-P-1
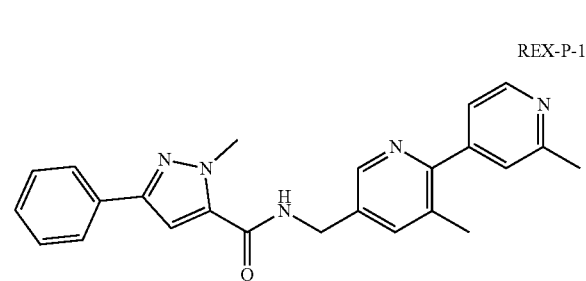
REX-P-2
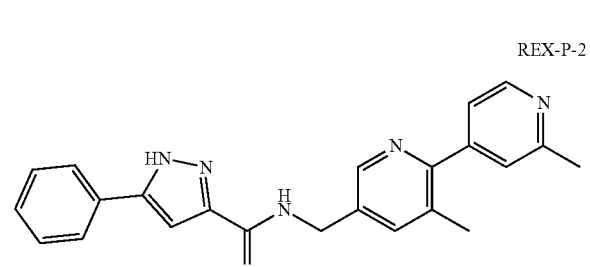
REX-P-3
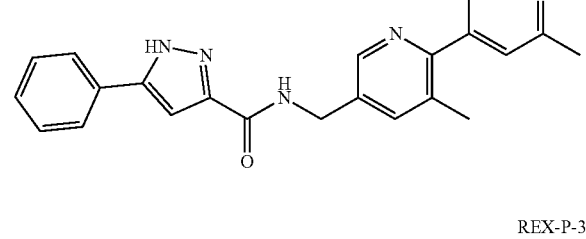
REX-P-4
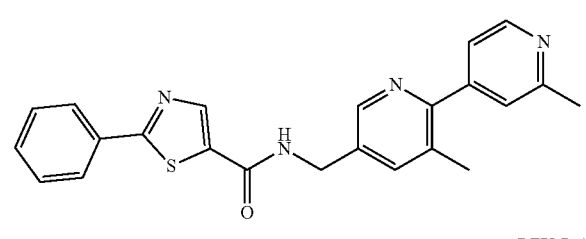
REX-P-5
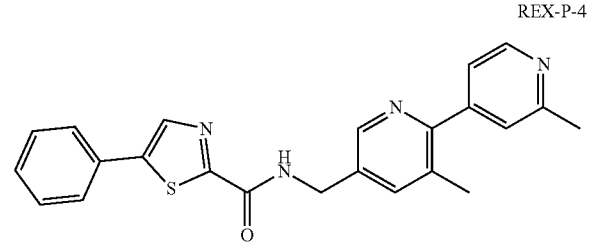
REX-P-6
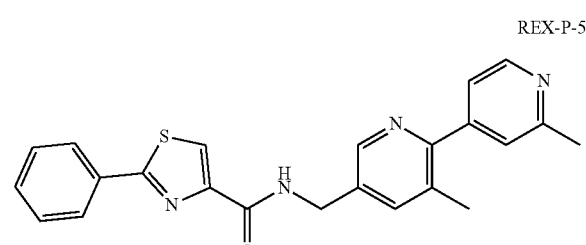
REX-P-7
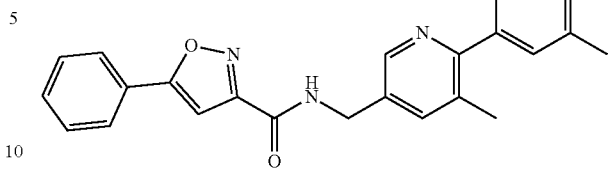
REX-P-8
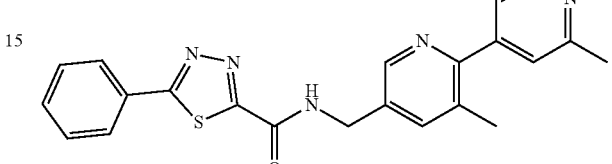
REX-P-9
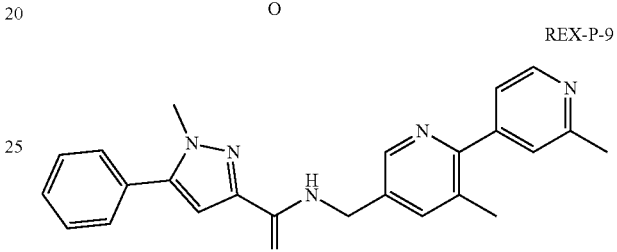
REX-P-10
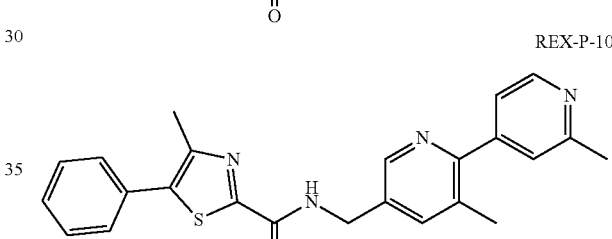
REX-P-11
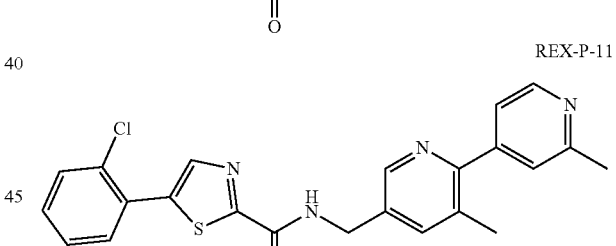
REX-P-12
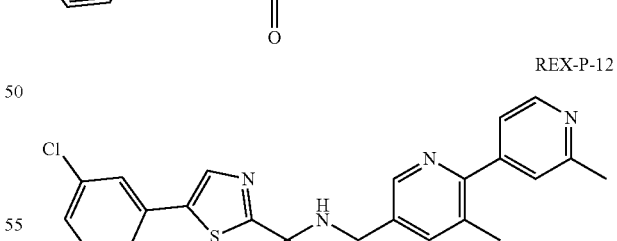
REX-P-13
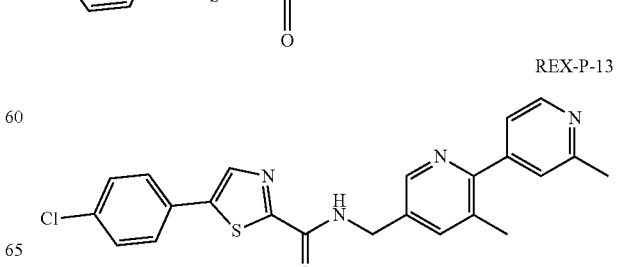

REX-P-14
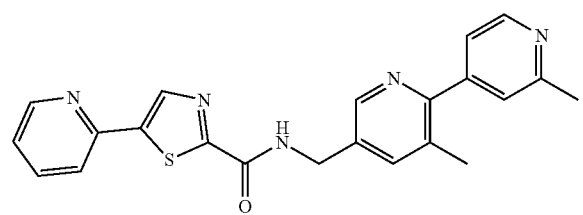
REX-P-20
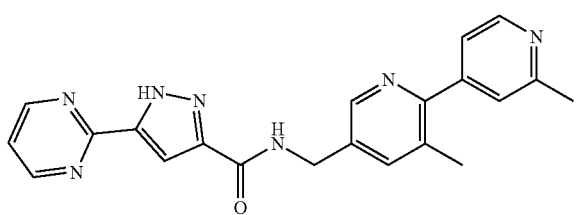
REX-P-15
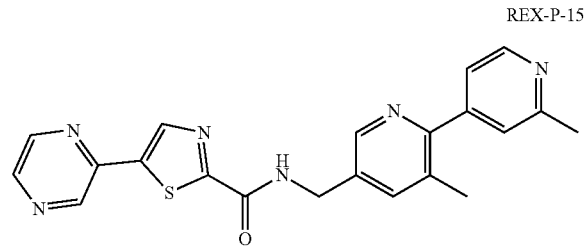
REX-P-21
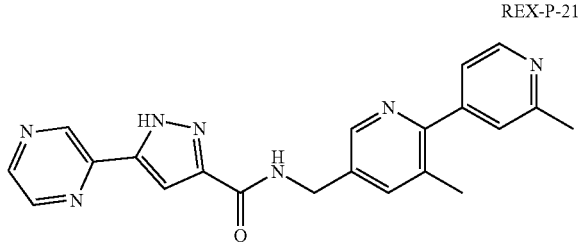
REX-P-16
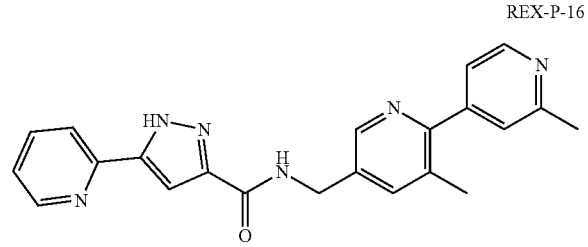
REX-P-22
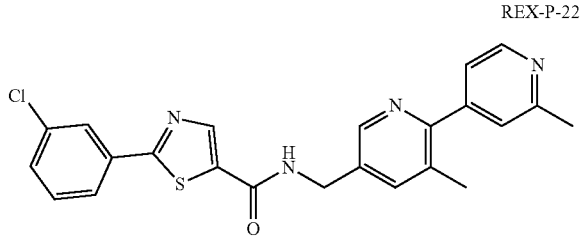
REX-P-17
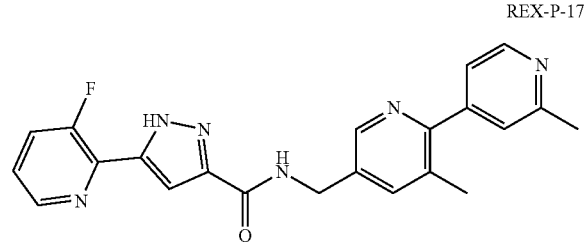
REX-P-23
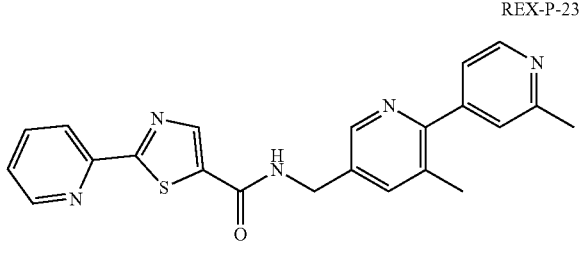
REX-P-18
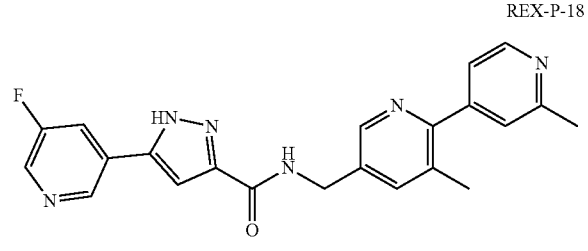
REX-P-24
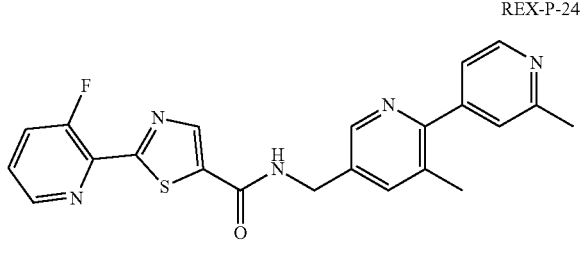
REX-P-19
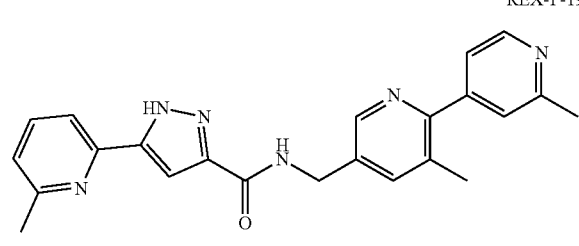
REX-P-25
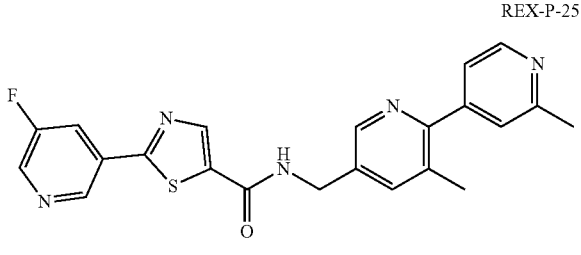

REX-P-26
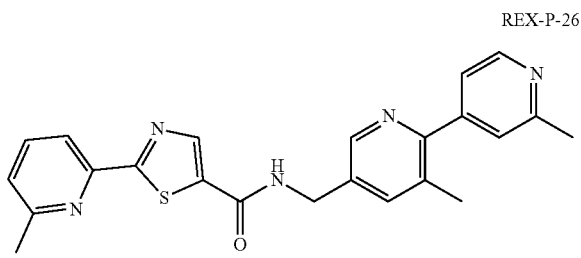
REX-P-32
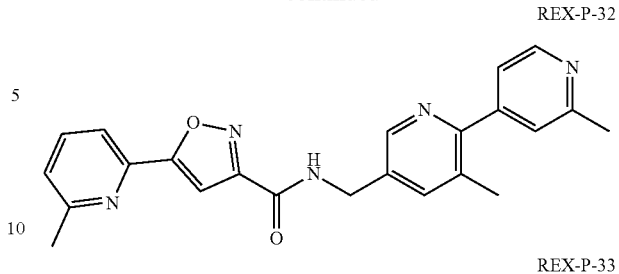
REX-P-27
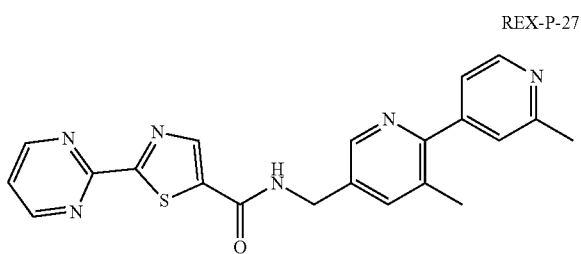
REX-P-33
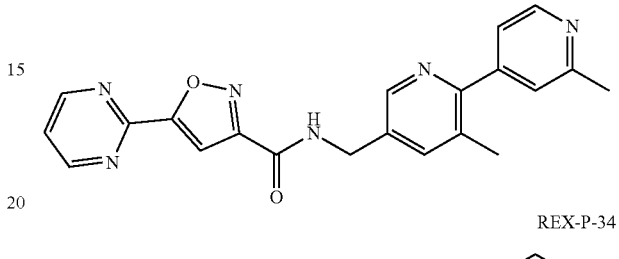
REX-P-28
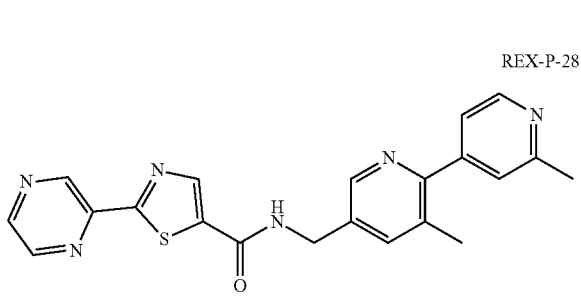
REX-P-34
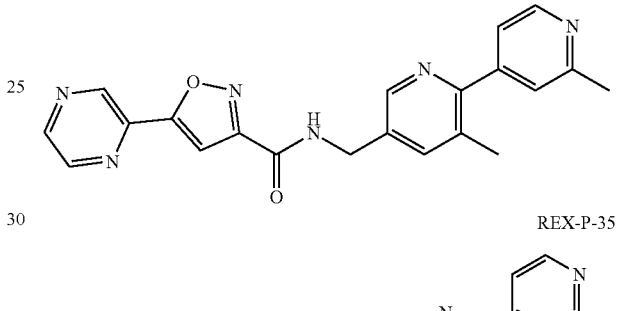
REX-P-29
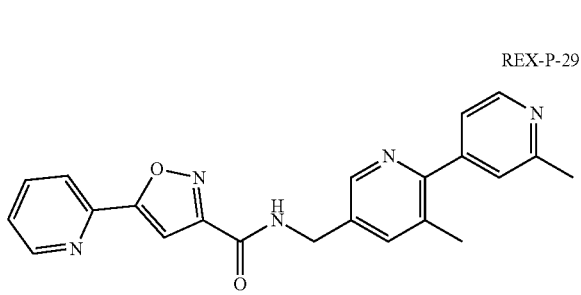
REX-P-35
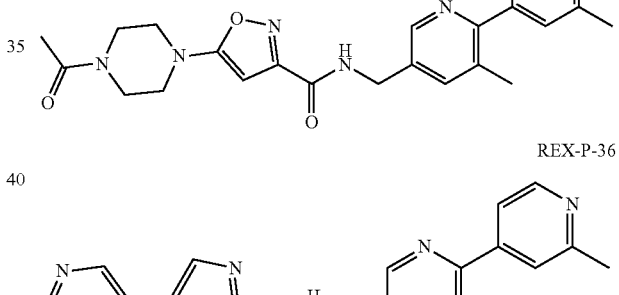
REX-P-30
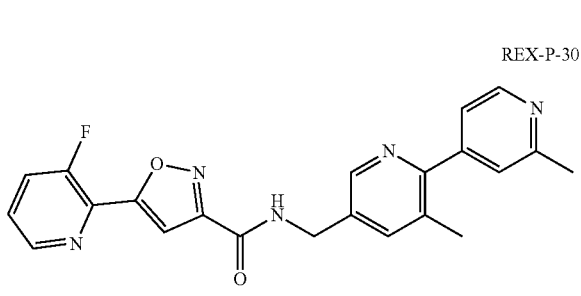
REX-P-36
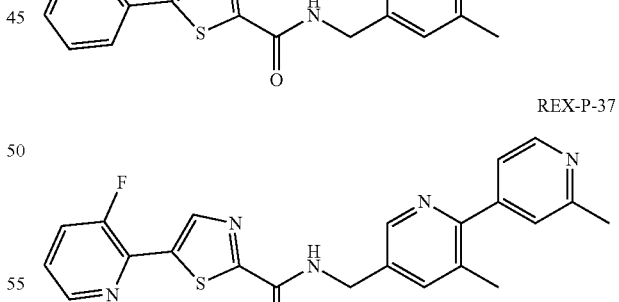
REX-P-31
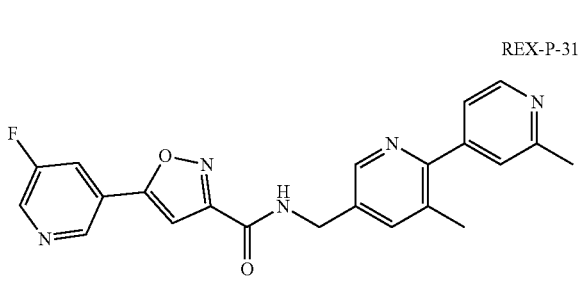
REX-P-37
REX-P-38
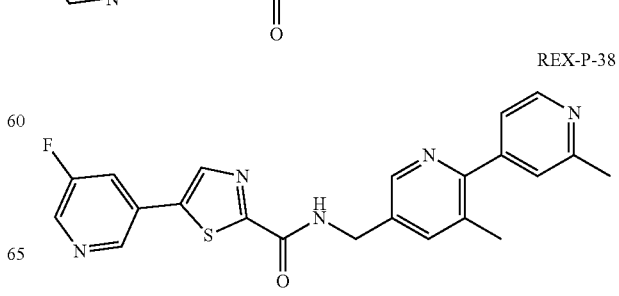

REX-P-39
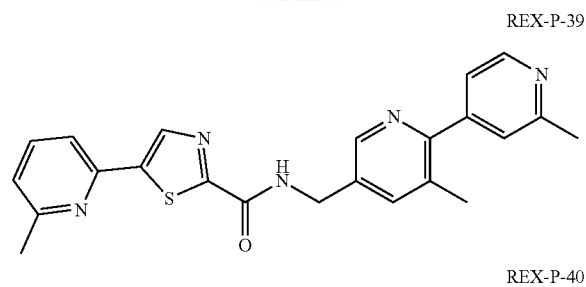
REX-P-40
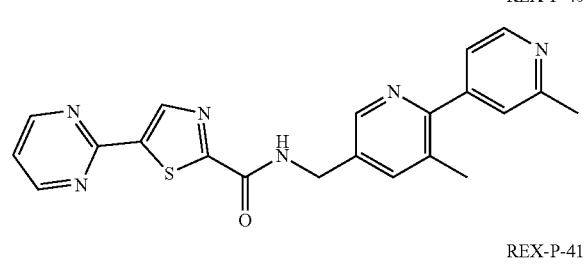
REX-P-41
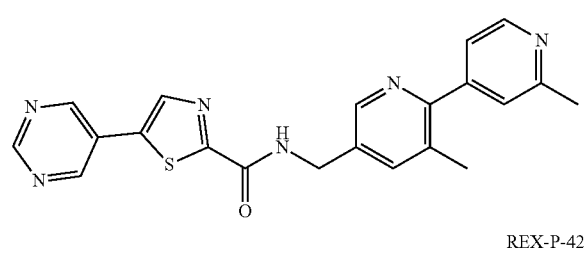
REX-P-42
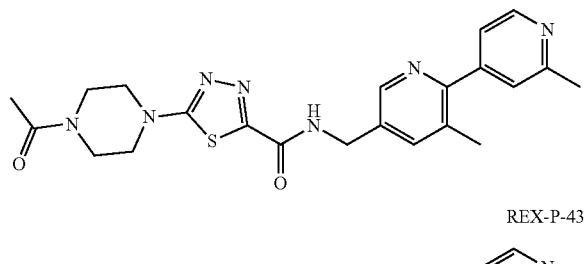
REX-P-43
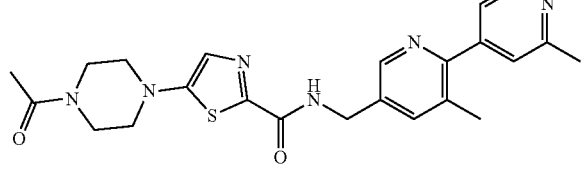
REX-P-44
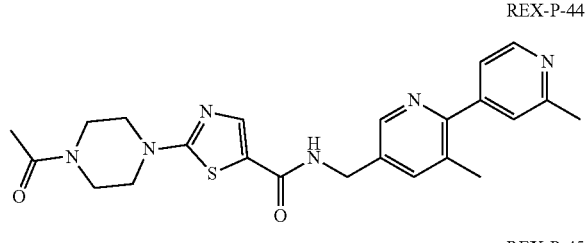
REX-P-45
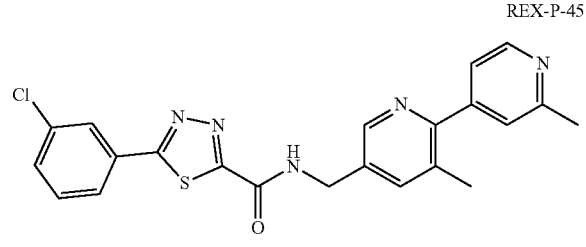
REX-P-46
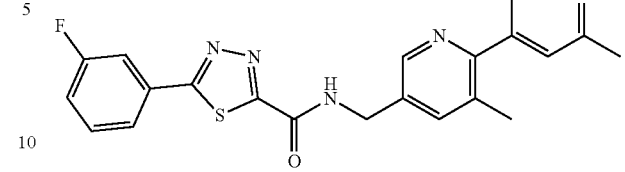
REX-P-47
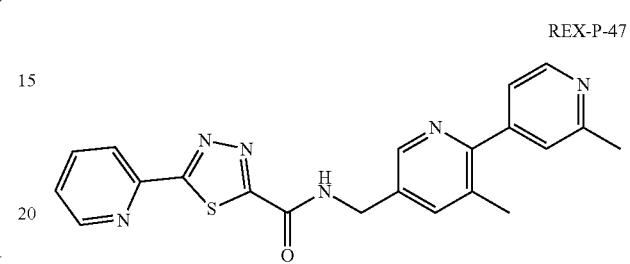
REX-P-48
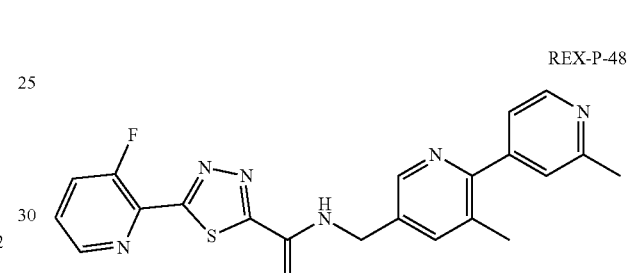
REX-P-49
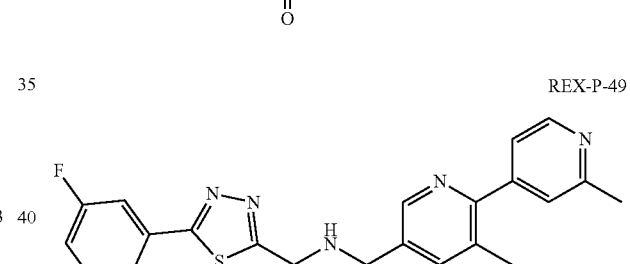
REX-P-50
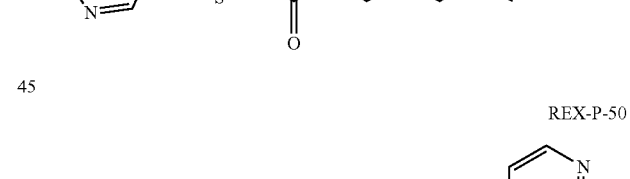
REX-P-51
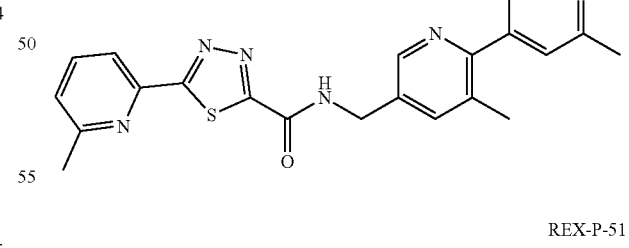

-continued

REX-P-52
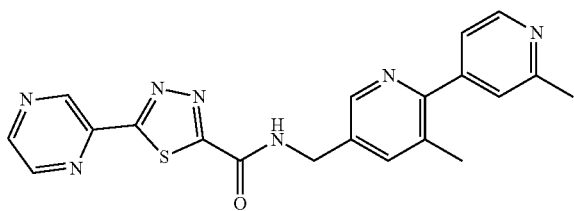

REX-P-53
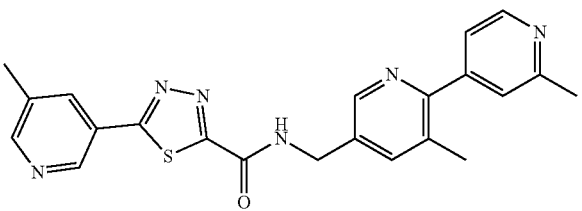

REX-P-54
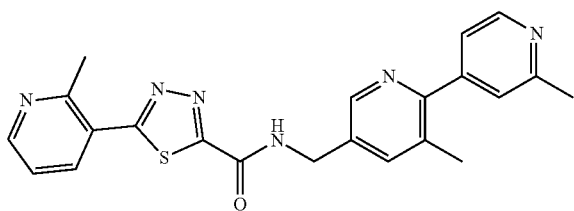

REX-P-55
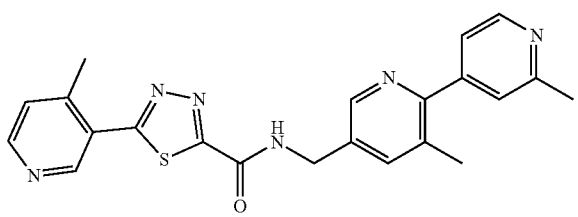

REX-P-56
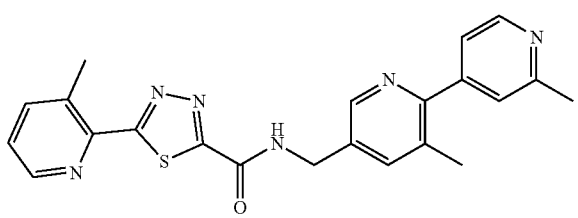

The "compound" of the present invention comprises all stereoisomers, geometric isomers, tautomers, and isotopes.

The "compound" of the present invention may be asymmetric, for example, having one or more stereoisomers. Unless otherwise indicated, all stereoisomers, such as enantiomers and diastereomers, are included. Compounds containing asymmetric carbon atoms in the present invention can be isolated in an optically active pure or racemic form. The optically pure form can be resolved from a racemic mixture or synthesized by using chiral starting materials or chiral reagents.

The "compound" of the present invention also includes tautomeric forms. Tautomeric forms result from the exchange between a single bond and an adjacent double bond, and which exchange is accompanied by the migration of a proton.

The present invention also comprises all isotope atoms, whether in an intermediate or a final compound. Isotope atoms include those having the same atomic number but different mass number. For example, the isotopes of hydrogen include deuterium and tritium.

For compounds containing the foregoing general structures, the terms used herein have the following meanings:

The term "halogen" refers to fluorine, chlorine, bromine or iodine, preferably fluorine, chlorine or bromine.

The term "cyano" refers to —CN.

The term "hydroxy" refers to —OH.

The term "alkyl" refers to a linear or branched saturated hydrocarbon group consisting of carbon atoms and hydrogen atoms, for example, $C_{1-20}$ alkyl, and preferably $C_{1-6}$ alkyl, such as methyl, ethyl, propyl (including n-propyl and isopropyl), butyl (including n-butyl, isobutyl, sec-butyl or t-butyl), pentyl (including n-pentyl, isopentyl and neopentyl), n-hexyl, 2-methylhexyl and the like. The alkyl group may be unsubstituted or substituted with one or more substituent(s) including, but not limited to, alkyl, alkoxy, cyano, hydroxy, carbonyl, carboxyl, aryl, heteroaryl, amino, halogen, sulfonyl, sulfinyl, and phosphoryl.

The term "amino" refers to —$NH_2$, —NH(alkyl), and —N(alkyl)$_2$, the meaning of alkyl being as previously provided. The structural form of —NH(alkyl) is

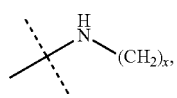

and specific examples include, but not limited to, —$NHCH_3$, —$NHCH(CH_3)_2$, —$NHC_2H_5$, and the like; and the structural form of —N(alkyl)$_2$ is

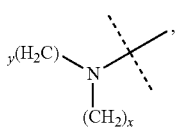

and specific examples include, but are not limited to, —$N(CH_3)_2$, —$N(CH_3)C_2H_5$, and the like.

The term "aryl" refers to an all-carbon monocyclic or fused ring having a completely conjugated π-electron system with generally 6-14 carbon atoms, preferably 6 to 12 carbon atoms, and most preferably 6 carbon atoms. The aryl can be unsubstituted or substituted with one or more substituent(s including, but not limited to, alkyl, alkoxy, cyano, hydroxy, carbonyl, carboxyl, aryl, aralkyl, amino, halogen, sulfonyl, sulfinyl, and phosphoryl. Examples of unsubstituted aryl include, but are not limited to, phenyl, naphthyl, and anthryl.

The term "heterocyclyl" refers to a monocyclic or fused ring having 3 to 12 (integer) ring atoms, wherein 1, 2 or 3 ring atom(s) is(are) selected from one or more of N and O, and the other ring atoms are C, and having a completely conjugated π-electron system. The heterocyclyl can be a saturated or unsaturated group, and also can be unsubstituted or substituted with one or more substituent(s), including but not limited to alkyl, alkoxy, cyano, hydroxy, carbonyl, carboxyl, aryl, aralkyl, amino, halogen, sulfonyl, sulfinyl, and phosphoryl. Examples of unsubstituted heterocyclyl include, but are not limited to, pyrrolyl, indolyl, pyrrolidinyl, imidazolyl, pyrazolyl, tetrazolyl, pyridyl, quinolyl, isoquinolyl, piperidyl, pyrimidyl, pyrazinyl, piperazinyl, furyl, pyranyl, and morpholinyl.

The present invention also provides a pharmaceutical composition, comprising the compound or a pharmaceutically acceptable salt thereof as described above as an active ingredient, and one or more pharmaceutically acceptable carriers.

The "pharmaceutical composition" of the present invention refers to a formulation consisting of one or more compounds of the present invention, or salts thereof, and a carrier that is generally accepted in the art for the delivery of biologically active compounds to an organism (such as human). The purpose of the pharmaceutical composition is to facilitate the drug delivery to the organism.

The term "pharmaceutically acceptable carrier" refers to a substance that is administered together with the active ingredient and beneficial to the administration of the active ingredient, including, but not limited to, any glidants, sweetening agents, diluents, preservatives, dyes/colorants, flavor enhancers, surfactants, wetting agents, dispersing agents, disintegrating agents, suspending agents, stabilizers, isotonic agents, solvents, or emulsifiers, which are licensed by the State Food and Drug Administration and acceptable for human or animal (such as livestock). Examples of the carrier include, but are not limited to, calcium carbonate, calcium phosphate, various sugars and various types of starch, cellulose derivatives, gelatin, vegetable oil, and polyethylene glycol.

The pharmaceutical composition of the present invention may be formulated into solid, semi-solid, liquid or gaseous formulations, such as tablets, pills, capsules, powders, granules, pastes, emulsions, suspensions, solutions, suppositories, injections, inhalants, gels, microspheres, and aerosols, and the like.

The pharmaceutical composition of the present invention may be manufactured using the method well known in the art, such as conventional mixing method, dissolution method, granulation method, dragee manufacture method, grinding method, emulsion method, lyophilization, and the like.

The routes of administration of the compound of the present invention, or a pharmaceutically acceptable salt thereof, or a pharmaceutical composition thereof include, but are not limited to, oral, rectal, transmucosal, and enteral administration, or topical, transdermal, inhalation, parenteral, sublingual, intravaginal, intranasal, intraocular, intraperitoneal, intramuscular, subcutaneous, and intravenous administration. The preferred route of administration is oral administration.

For oral administration, the active compounds may be mixed with pharmaceutically acceptable carriers well-known in the art to formulate the pharmaceutical composition. These carriers enable the compounds of the present invention to be formulated as tablets, pills, lozenges, dragees, capsules, liquids, gels, syrups, suspending agents, or the like, for oral administration to a patient. For example, a pharmaceutical composition for oral administration may be obtained as a tablet by using the following method: combining the active ingredient with one or more solid carriers, if necessary, granulating the resulting mixture, and if necessary, adding a small amount of excipients for processing same into a mixture or granules, so as to form a tablet or tablet core. The tablet core may be combined with a optionally coating material suitable for enteric dissolution, and processed into a coating formulation form that is more favourable for absorption by organisms (such as human).

The present invention also provides the use of the compound or a pharmaceutically acceptable salt thereof as described above in the preparation of drugs antagonizing the Wnt signaling pathway.

Preferably, the use in the preparation of drugs is for the treatment of cell proliferative diseases and digestive system diseases associated with abnormal Wnt signaling activity.

More preferably, the use in the preparation of drugs is for the treatment of cancer, including non-small cell lung cancer, anaplastic large cell lymphoma, inflammatory myofibroblastic tumor, nasopharyngeal cancer, breast cancer, colorectal cancer, diffuse large B-cell lymphoma, liver cancer, gastric cancer, esophageal cancer, pancreatic cancer, ovarian cancer, systemic histiocytosis, and neuroblastoma.

In the present invention, the inventors measured the inhibitory activity against STF reporter genes of the Wnt pathway at the molecular level for a series of synthesized five-membered heterocyclic amide Wnt pathway inhibitors obtained, and found that some compounds have a significant inhibitory activity against the Wnt pathway. In addition, a zebrafish phenotype screening assay was conducted, and through the inhibition assay of resected-tail regeneration of zebrafish and the axin formation inhibition assay, it was found that some compounds had significant anti-tumor activity in vivo; Furthermore, the compounds were proved to have significant anti-tumor effects by in vivo pharmacodynamic assays.

Compared with the prior art, the five-membered heterocyclic amide Wnt pathway inhibitor provided by the present invention is based on target-based rational drug design, and a series of novel compounds are obtained through the substitution and modification of groups; and with the STF reporter gene assay and zebrafish phenotype screening assay, a series of compounds having an anti-tumor activity are optimized and screened. Therefore, these compounds can be used to develop a new generation of Wnt pathway inhibitors, which have great clinical application value for targeted therapy or prevention of diseases mediated by the Wnt pathway, and have a considerable market potential.

EXAMPLES

Figure 1:
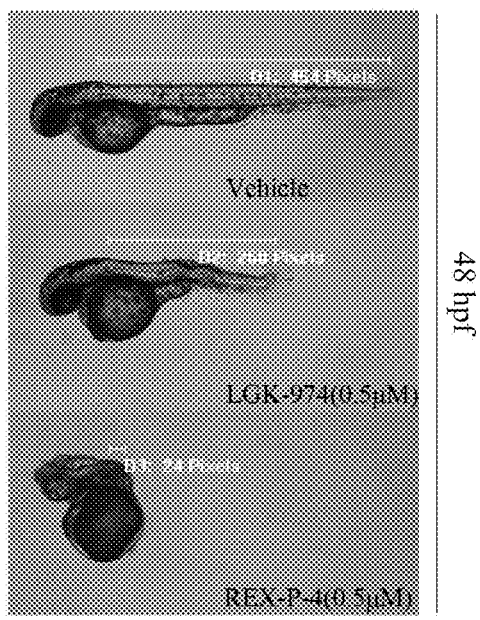
FIG. 1 is a diagram showing the growth inhibition of the axis formation of AB type zebrafish after 48 h treatment

The following are specific embodiments of the present invention, and further describe the technical solutions of the present invention, but the scope of the present invention is not limited to these embodiments. Any changes or equivalent substitutions without departing from the concept of the present invention are included in the scope of protection of the present invention.

In the method for preparing the target compound provided by the present invention, the liquid chromatograph adopted a Waters Symmetry C18 column. TLC using GF254 (0.25 mm). Nuclear Magnetic Resonance spectroscopy (NMR) was determined using a Bruker-400 nuclear magnetic resonance instrument; liquid chromatograph-mass spectroscopy (LC/MS) was performed using a Waters ZQ mass spectrometer detector (column: Waters Symmetry C18, mm, 5 micron, 35° C.) in ESI (+) ion mode.

In addition, all operations involving easily oxidizable or easily hydrolyzed materials are carried out under nitrogen protection. Unless otherwise specified, the starting materials used in the present invention are commercially available materials and can be used without further purification.

Example 1

N-((2',3-dimethyl-[2,4'-bipyridin]-5-yl)methyl)-5-phenyl-1H-pyrazole-3-carboxamide [No. REX-P-2]

Synthetic Routes:

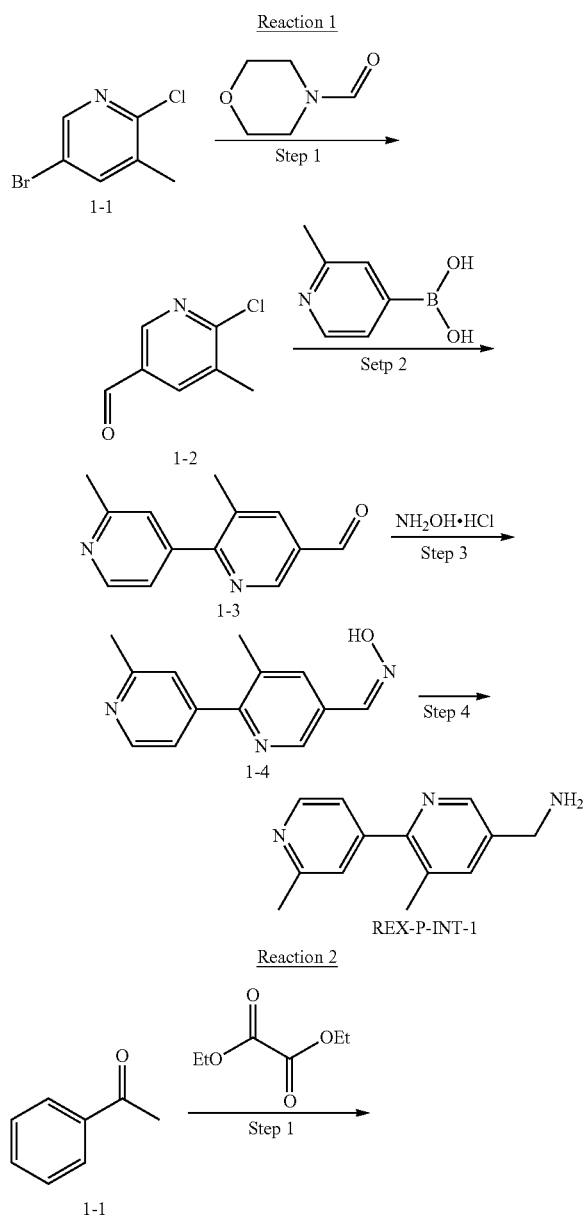

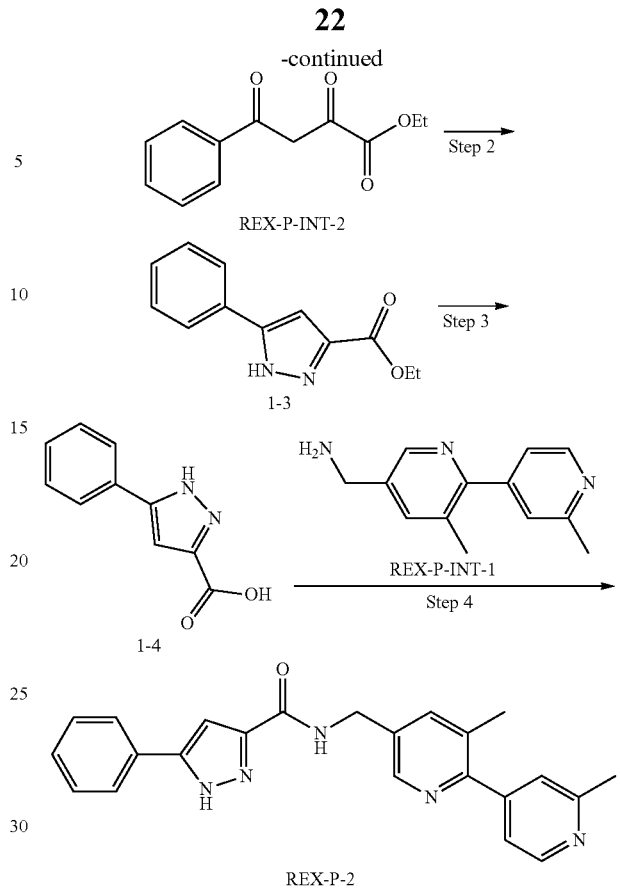

Reaction 1: the Preparation of the Compound REX-P-INT-1

Step 1: Preparation of compound 1-2 cc

To a solution of 1-1 (5 g, 24.2 mmol) in THF (200 mL) was added drop-wise isopropyl magnesium chloride (12.7 mL, 25.5 mmol) in THF at 0° C. The mixture was stirred at room temperature for 1 h. A solution of morpholine-4-carbaldehyde (2.5 mL, 24.2 mmol) in THF (50 ml) was added drop-wise into the mixture slowly and the mixture was stirred at same temperature for 1 h. The solution was poured into ice water and extracted with EtOAc. The combined organic layer was washed with brine, dried over anhydrous $Na_2SO_4$, filtered concentrated under reduced pressure to give the crude product. The crude product was purified by silica gel chromatography eluted to give product 1-2 (3.0 g, 79.6%).

MS m/z [ESI]: 156.0 [M+1].

Step 2: Preparation of Compound 1-3

To a solution of 1-2 (3.0 g, 19.4 mmol) and (2-methyl-pyridin-4-yl)boronic acid (3.2 g, 23.2 mmol) in DMF (200 mL) was added $K_2CO_3$ (10.7 g, 77.6 mmol) and $Pd(PPh_3)_4$ (1.1 g 1.0 mmol) at $N_2$ atmosphere. Then the reaction mixture was stirred at 100° C. under $N_2$ atmosphere overnight. The solution was poured into ice water (200 mL) and extracted with EtOAc. The organic layer was washed with brine, filtered and concentrated under reduced pressure to give the crude product. The crude product was purified by silica gel chromatography eluted to give product 1-3 (1.8 g, 44.0%).

MS m/z [ESI]: 213.1 [M+1].

Step 3: Preparation of Compound 1-4

To a solution of 1-3 (1.8 g, 8.5 mmol) in EtOH (50 mL) was added hydroxylamine hydrochloride (1.2 g, 17.0 mmol) and NaOAc (1.4 g, 17.0 mmol). The reaction mixture was stirred at room temperature for 2 hours. The solution was poured into ice water (50 mL), extracted with EtOAc, washed with brine, dried with anhydrous Na$_2$SO$_4$, filtered and concentrated to give the crude product. The crude product was purified by silica gel chromatography eluted to give product 1-4 (1.8 g, 93.4%).

MS m/z [ESI]: 228.1 [M+1].

Step 4: Preparation of Compound REX-P-INT-1

To a solution of 1-4 (1.8 g, 7.9 mmol) in EtOH (30 mL) was added 10% Pd/C (0.2 g) and aqueous HCl (1.5 mL, 12 N). The reaction mixture was stirred under H$_2$ atmosphere at room temperature overnight. The mixture was filtered and concentrated to give the target compound REX-P-INT-1 (1.4 g, 85.2%).

MS m/z [ESI]: 214.1 [M+1].

Reaction 2: the Preparation of the Compound REX-P-2

Step 1: Preparation of compound REX-P-INT-2

To a solution of NaH (1.2 g, 50.0 mmol) in DMF (30 mL) a solution of 1-1 (5.0 g, 42.0 mmol) and diethyl oxalate (56.9 mL, 420.0 mmol) in DMF (100 mL) was added drop-wise into the mixture. The reaction mixture was stirred at 50° C. for 2 hours. The solution was poured into ice water (200 mL), extracted with EtOAc, washed with brine, dried with anhydrous Na$_2$SO$_4$, filtered and concentrated to give the crude product. The crude product was purified by silica gel chromatography eluted to give product REX-P-INT-2 (8.6 g, 92.8%).

MS m/z [ESI]: 221.1 [M+1].

Step 2: Preparation of Compound 1-3

To a solution of REX-P-INT-2 (8.6 g, 39.1 mmol) in EtOH (50 mL) was added hydrazine hydrate (2.3 g, 46.9 mmol). The reaction mixture was stirred at room temperature for 5 hours. The reaction mixture was poured into aqueous solution of sodium bicarbonate (100 mL), extracted with EtOAc, washed with brine, dried with anhydrous Na$_2$SO$_4$, filtered and concentrated to give the crude product. The crude product was purified by silica gel chromatography eluted to give product 1-3 (3.4 g, 40.7%).

MS m/z [ESI]: 217.1 [M+1].

Step 3: Preparation of Compound 1-4

To a solution of 1-3 (3.4 g, 15.9 mmol) in MeOH (40 mL) was added NaOH (140 mL, 4M). The reaction mixture was stirred at room temperature for 2 hours. The reaction mixture was concentrated under reduced pressure to remove MeOH. The aqueous phase was acidified with aqueous HCl (1 M) till pH=3 and the mixture was extracted with EtOAc, dried with anhydrous Na$_2$SO$_4$, filtered and concentrated to give the crude product. The crude product was purified by silica gel chromatography eluted to give product 1-4 (2.4 g, 80.4%).

MS m/z [ESI]: 189.1 [M+1].

Step 4: Preparation of Compound REX-P-2

To a solution of 1-4 (2.4 g, 12.8 mmol) and REX-P-INT-1 (2.7 g, 12.8 mmol) in DMSO (50 mL) was added N-ethyldiisopropylamine (6.3 mL, 38.4 mmol) and 2-(7-Aza-1H-benzotriazole-1-yl)-1,1,3,3-tetramethyluronium hexafluorophosphate (5.8 g, 15.4 mmol). The reaction mixture was stirred at room temperature for 2 hours. The solution was poured into ice water (200 mL), extracted with EtOAc, dried with anhydrous Na$_2$SO$_4$, filtered and concentrated to give the crude product. The crude product was purified by silica gel chromatography eluted to give product REX-P-2 (3.0 g, 61.3%).

MS m/z [ESI]: 384.2 [M+1].

$^1$H-NMR (400 MHz, DMSO-d$_6$): δ=13.79 (s, 1H), 8.85-9.36 (m, 1H), 8.48-8.54 (m, 2H), 7.65-7.85 (m, 3H), 7.30-7.50 (m, 5H), 7.10 (s, 1H), 4.45-4.58 (m, 2H), 2.53 (s, 3H), 2.33 (s, 3H).

Example 2

N-((2',3-dimethyl-[2,4'-bipyridin]-5-yl)methyl)-2-phenylthiazole-5-carboxamide [REX-P-3]

Synthetic Routes:

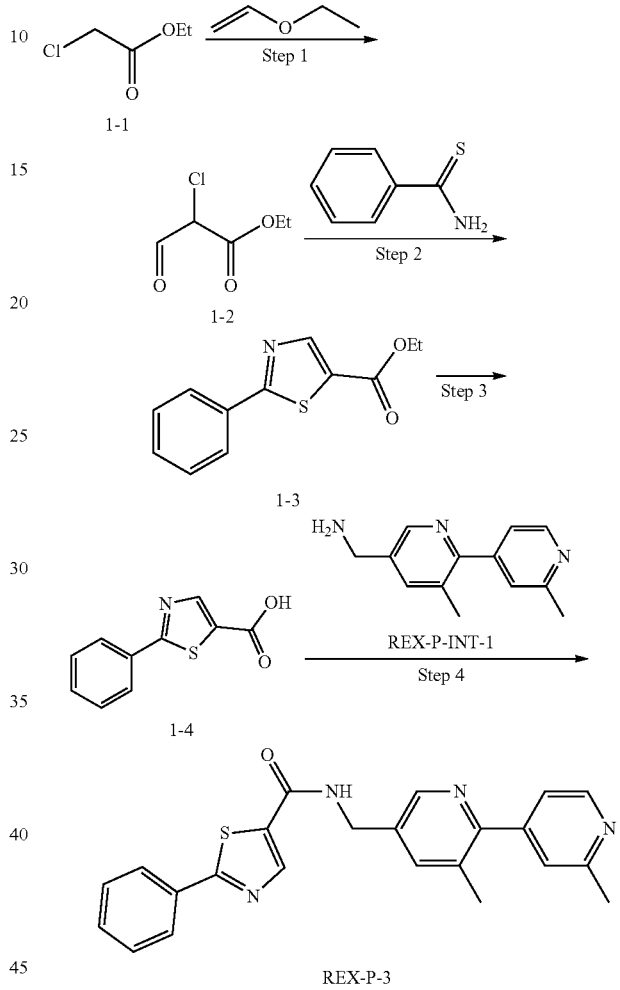

Step 1: Preparation of Compound 1-2

To a solution of ethyl 2-chloroacetate (5.0 g, 40.9 mmol) and ethyl formate (3.0 g, 40.9 mmol) in toluene (100 mL) was added sodium ethoxide (3.3 g, 48.5 mmol) at 0° C. The reaction mixture was stirred at 0° C. for 5 hours, the mixture was warmed up to room temperature stirred for 12 hours. The mixture was quenched with ice water (200 mL), extracted with Ether, washed with brine, dried with anhydrous Na$_2$SO$_4$, filtered and concentrated to give the crude product. The crude product was purified by silica gel chromatography eluted to give product 1-2 (4.5 g, 73.3%).

MS m/z [ESI]: 151.0 [M+1].

Step 2: Preparation of Compound 1-3

To a solution of 1-2 (4.5 g, 30.0 mmol) and thiobenzamide (4.1 g, 30.0 mmol) in toluene (50 mL) was added magnesium sulfate heptahydrate (7.2 g, 59.8 mmol). The reaction mixture was stirred at 100° C. for 4 hours and quenched with ice water (100 mL), extracted with ether, washed with brine, dried with anhydrous Na$_2$SO$_4$, filtered and concentrated to give the crude product. The crude product was purified by silica gel chromatography eluted to give product 1-3 (3.2 g, 45.9%).

MS m/z [ESI]: 234.1 [M+1].

Step 3: Preparation of Compound 1-4

To a solution of 1-3 (3.2 g, 13.8 mmol) in MeOH (50 mL) was added Sodium hydroxide solution (130 mL, 4 M). The reaction mixture was stirred at room temperature for 2 hours and concentrated under reduced pressure to remove MeOH. The aqueous phase was acidified with aqueous HCl (1 M) till pH=3 and the mixture was extracted with EtOAc, dried with anhydrous $Na_2SO_4$, filtered and concentrated to give the crude product. The crude product was purified by silica gel chromatography eluted to give product 1-4 (2.3 g, 81.8%).

MS m/z [ESI]: 206.0 [M+1].

Step 4: Preparation of Compound REX-P-3

According to the reaction 1 in example 1 to give the intermediate compound REX-P-INT-1 2.9 g.

To a solution of 1-4 (2.3 g, 11.3 mmol) and REX-P-INT-1 (2.9 g, 13.6 mmol) in DMSO (50 mL) was added N,N-Diisopropylethylamine (5.5 mL, 38.4 mmol) and o-(7-Azabenzotriazol-1-yl)-N,N,N',N'-te-tramethyluronium hexafluorophosphate (5.1 g, 13.6 mmol). The reaction mixture was stirred at room temperature for 2 hours and quenched with ice water (200 mL), extracted with EtOAc, washed with brine, dried with anhydrous $Na_2SO_4$, filtered and concentrated to give the crude product. The crude product was purified by silica gel chromatography eluted to give product REX-P-3 (2.8 g, 61.3%).

MS m/z [ESI]: 401.1 [M+1].

$^1$H-NMR (400 MHz, DMSO-$d_6$): δ=8.56 (d, J=5.2 Hz, 1H), 8.51 (d, J=2.0 Hz, 1H), 8.26 (s, 1H), 7.92-7.98 (m, 2H), 7.65-7.68 (m, 1H), 7.44-7.51 (m, 3H), 7.30 (s, 1H), 7.21-7.24 (m, 1H), 7.16 (t, J=6.0 Hz, 1H), 4.66 (d, J=6.0 Hz, 2H), 2.61 (s, 3H), 2.35 (s, 3H).

Example 3

N-((2',3-dimethyl-[2,4'-bipyridin]-5-yl)methyl)-5-phenylthiazole-2-carboxamide [REX-P-4]

Synthetic Routes:

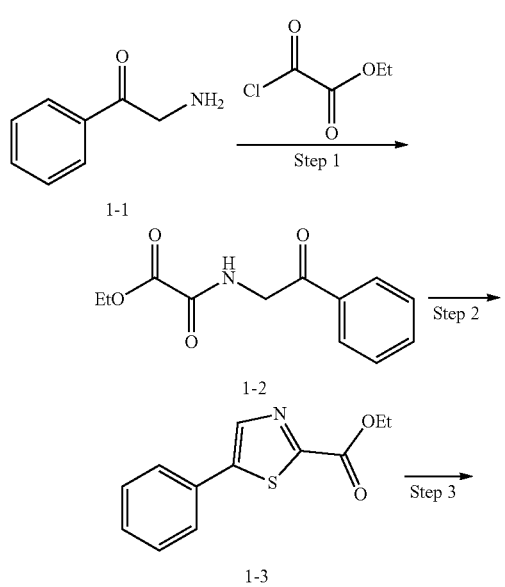

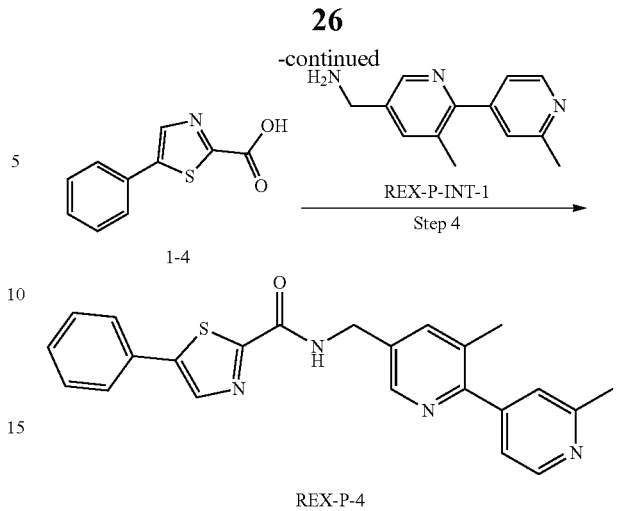

Step 1: Preparation of Compound 1-2

To a solution of 1-1 (5.0 g, 29.1 mmol) and triethylamine (8.5 mL, 61.1 mmol) in Dichloromethane was added dropwise ethyl oxalyl monochloride (4.4 g, 32.0 mmol). The reaction mixture was stirred at room temperature for 72 hours. The mixture was quenched with ice water (200 mL), extracted with dichloromethane, washed with brine, dried with anhydrous $Na_2SO_4$, filtered and concentrated to give the crude product. The crude product was purified by silica gel chromatography eluted to give product 1-2 (5.0 g, 73.0%).

MS m/z [ESI]: 236.1 [M+1].

Step 2: Preparation of Compound 1-3

To a solution of 1-2 (5.0 g, 21.3 mmol) in Trichloromethane (50 mL) was added phosphorus pentasulfide (9.0 g, 42.6 mmol). The reaction mixture was stirred at 60° C. overnight. The mixture was quenched with ice water (100 mL), extracted with dichloromethane, washed with brine, dried with anhydrous $Na_2SO_4$, filtered and concentrated to give the crude product. The crude product was purified by silica gel chromatography eluted to give product 1-3 (4.5 g, 90.8%).

MS m/z [ESI]: 234.1 [M+1].

Step 3: Preparation of Compound 1-4

To a solution of 1-3 (4.5 g, 19.3 mmol) in MeOH (80 mL) was added sodium hydroxide solution (150 mL, 4 M). The reaction mixture was stirred at room temperature for 2 hours and concentrated under reduced pressure to remove MeOH. The aqueous phase was acidified with aqueous HCl (1 M) till pH=3 and the mixture was extracted with EtOAc, dried with anhydrous $Na_2SO_4$, filtered and concentrated to give the crude product. The crude product was purified by silica gel chromatography eluted to give product 1-4 (3.3 g, 82.3%).

MS m/z [ESI]: 206.0 [M+1].

Step 4: Preparation of Compound REX-P-4

According to the reaction 1 in example 1 to give the intermediate compound REX-P-INT-1 3.6 g.

To a solution of 1-4 (3.3 g, 15.9 mmol) and REX-P-INT-1 (3.6 g, 17.0 mmol) in DMSO (50 mL) was added N,N-diisopropylethylamine (6.8 mL, 47.7 mmol) and o-(7-Azabenzotriazol-1-yl)-N,N,N',N'-te-tramethyluronium hexafluorophosphate (7.2 g, 19.1 mmol). The reaction mixture was stirred at room temperature for 2 hours and quenched with ice water (200 mL), extracted with EtOAc, washed with brine, dried with anhydrous $Na_2SO_4$, filtered and concentrated to give the crude product. The crude product was purified by silica gel chromatography eluted to give product REX-P-4 (2.3 g, 35.9%).

MS m/z [ESI]: 401.1 [M+1].

$^1$H-NMR (400 MHz, DMSO-d$_6$): δ=8.58 (d, J=5.2 Hz, 1H), 8.55 (d, J=2.0 Hz, 1 H), 7.99 (s, 1H), 7.78 (t, J=6.0 Hz, 1H), 7.65-7.68 (m, 1H), 7.58-7.62 (m, 2H), 7.37-7.47 (m, 3H), 7.32 (s, 1H), 7.22-7.25 (m, 1H), 4.70 (d, J=6.4 Hz, 2H), 2.63 (s, 3H), 2.36 (s, 3H).

Example 4

N-((2',3-dimethyl-[2,4'-bipyridin]-5-yl)methyl)-2-phenylthiazole-4-carboxamide [REX-P-5]

Synthetic Routes:

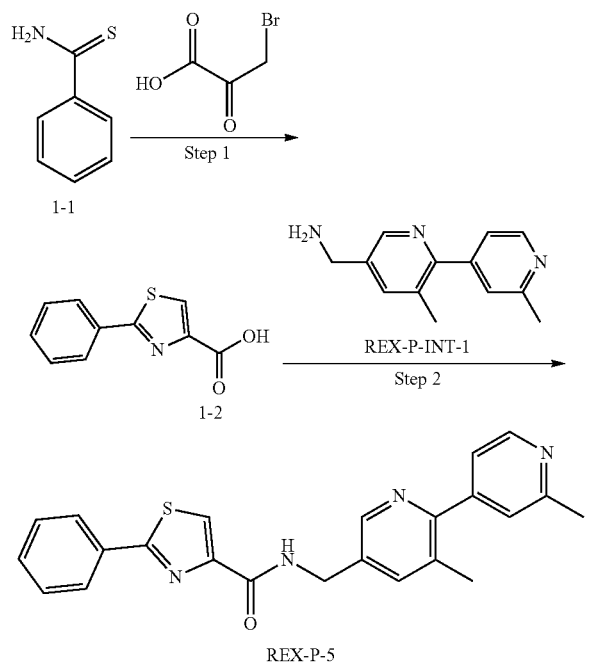

Step 1: Preparation of Compound 1-2

To a solution of 1-1 (1.0 g, 7.3 mmol) and 3-bromopyruvic acid (1.2 g, 7.3 mmol) in 1,4-dioxane (50 mL). The reaction mixture was stirred at 110° C. for 2 hours. The mixture was quenched with ice water (100 mL), extracted with EtOAc, washed with brine, dried with anhydrous Na$_2$SO$_4$, filtered and concentrated to give the crude product. The crude product was purified by silica gel chromatography eluted to give product 1-2 (0.8 g, 53.5).

MS m/z [ESI]: 206.0 [M+1].

Step 2: Preparation of Compound REX-P-5

According to the reaction 1 in example 1 to give the intermediate compound REX-P-INT-1 0.9 g.

To a solution of 1-2 (0.8 g, 3.9 mmol) and REX-P-INT-1 (0.9 g, 4.3 mmol) in DMSO (20 ml) was added N,N-diisopropylethylamine (1.7 mL, 11.7 mmol) and o-(7-azabenzotriazol-1-yl)-N,N,N',N'-te-tramethyluronium hexafluorophosphate (1.8 g, 4.7 mmol). The reaction mixture was stirred at room temperature for 2 hours and quenched with ice water (50 mL), extracted with EtOAc, washed with brine, dried with anhydrous Na$_2$SO$_4$, filtered and concentrated to give the crude product. The crude product was purified by silica gel chromatography eluted to give product REX-P-5 (0.7 g, 44.7%).

MS m/z [ESI]: 401.1 [M+1].

$^1$H-NMR (400 MHz, DMSO-d$_6$): δ=9.20 (t, J=6.0 Hz, 1H), 8.51-8.55 (m, 2H), 8.35 (s, 1H), 8.05-8.11 (m, 2H), 7.72 (s, 1H), 7.53-7.57 (m, 3H), 7.40 (s, 1H), 7.34 (d, J=4.8 Hz, 1H), 4.57 (d, J=6 Hz, 2H), 2.53 (s, 3H), 2.35 (s, 3H).

Example 5

N-((2',3-dimethyl-[2,4'-bipyridin]-5-yl)methyl)-4-phenylthiazole-2-carboxamide [REX-P-6]

Synthetic Routes:

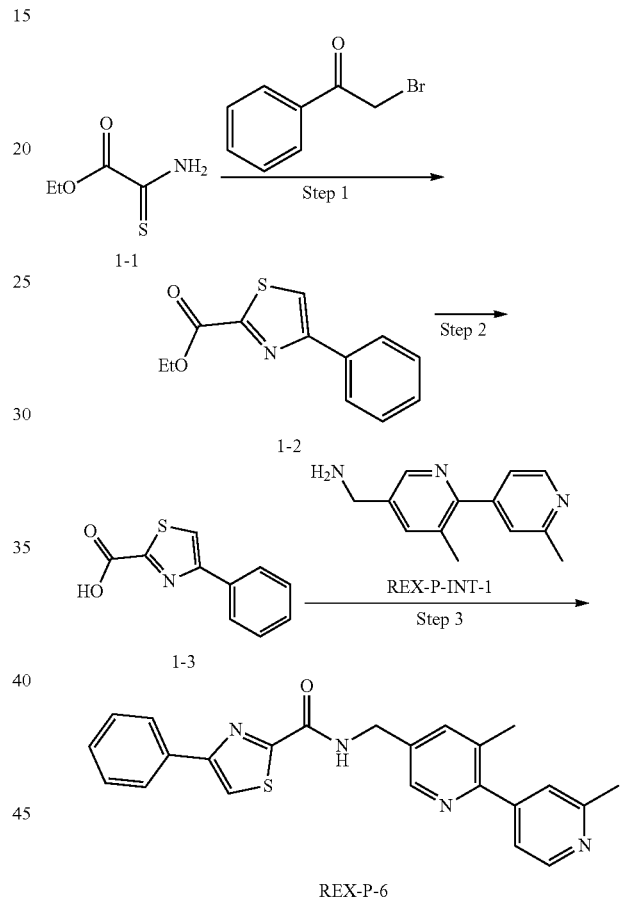

Step 1: Preparation of Compound 1-2

To a solution of 1-1 (1.0 g, 7.5 mmol) and 2-bromoacetophenone (1.5 mL, 7.5 mmol) in Benzol (80 mL) and EtOH (10 mL). The reaction mixture was stirred at room temperature for 18 hours and warmed up to 60° C. stirred for 2 hours. The reaction mixture was poured into aqueous solution of sodium bicarbonate (100 mL), extracted with EtOAc, washed with brine, dried with anhydrous Na$_2$SO$_4$, filtered and concentrated to give the crude product. The crude product was purified by silica gel chromatography eluted to give product 1-2 (0.9 g, 51.4%).

MS m/z [ESI]: 234.1 [M+1].

Step 2: Preparation of Compound 1-3

To a solution of 1-2 (0.9 g, 3.9 mmol) in MeOH (10 mL) was added sodium hydroxide solution (20 mL, 4 M). The reaction mixture was stirred at room temperature for 2 hours and concentrated under reduced pressure to remove MeOH. The aqueous phase was acidified with aqueous HCl (1 M) till pH=3 and the mixture was extracted with EtOAc, dried with anhydrous Na$_2$SO$_4$, filtered and concentrated to give the crude product. The crude product was purified by silica gel chromatography eluted to give product 1-3 (0.7 g, 88.3%).

MS m/z [ESI]: 206.0 [M+1].

Step 3: Preparation of Compound REX-P-6

According to the reaction 1 in example 1 to give the intermediate compound REX-P-INT-1 0.8 g.

To a solution of 1-3 (0.7 g, 3.4 mmol) and REX-P-INT-1 (0.8 g, 3.7 mmol) in DMSO (10 mL) was added N,N-diisopropylethylamine (1.5 mL, 11.2 mmol) and o-(7-Azabenzotriazol-1-yl)-N,N,N',N'-tetramethyluronium hexafluorophosphate (1.7 g, 4.4 mmol). The reaction mixture was stirred at room temperature for 2 hours and quenched with ice water (200 mL), extracted with EtOAc, washed with brine, dried with anhydrous Na$_2$SO$_4$, filtered and concentrated to give the crude product. The crude product was purified by silica gel chromatography eluted to give product REX-P-6 (0.5 g, 37.5%).

MS m/z [ESI]: 401.1 [M+1].

$^1$H-NMR (400 MHz, DMSO-d$_6$): δ=9.55 (t, J=6.4 Hz, 1H), 8.51-8.55 (m, 2H), 8.43 (s, 1H), 8.07-8.11 (m, 2H), 7.74 (d, J=1.6 Hz, 1H), 7.46-7.52 (m, 2H), 7.38-7.43 (m, 2H), 7.32-7.35 (m, 1H), 4.57 (d, J=6.4 Hz, 2H), 2.53 (s, 3H), 2.34 (s, 3H).

Example 6

N-((2',3-dimethyl-[2,4'-bipyridin]-5-yl)methyl)-5-phenylisoxazole-3-carboxamide [REX-P-7]

Synthetic Routes:

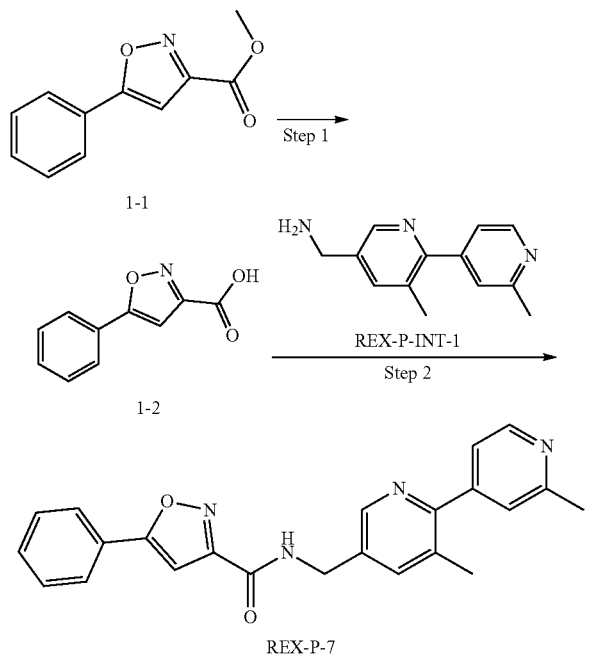

Step 1: Preparation of Compound 1-2

To a solution of 1-2 (1.0 g, 4.9 mmol) in MeOH (10 mL) was added sodium hydroxide solution (20 mL, 4 M). The reaction mixture was stirred at room temperature for 2 hours and concentrated under reduced pressure to remove MeOH. The aqueous phase was acidified with aqueous HCl (1 M) till pH=3 and the mixture was extracted with EtOAc, dried with anhydrous Na$_2$SO$_4$, filtered and concentrated to give the crude product. The crude product was purified by silica gel chromatography eluted to give product 1-2 (0.7 g, 79.5%).

MS m/z [ESI]: 190.0 [M+1].

Step 2: Preparation of Compound REX-P-7

According to the reaction 1 in example 1 to give the intermediate compound REX-P-INT-1 0.9 g.

To a solution of 1-2 (0.7 g, 3.9 mmol) and REX-P-INT-1 (0.9 g, 4.3 mmol) in DMSO (10 mL) was added N,N-diisopropylethylamine (1.6 mL, 11.7 mmol) and o-(7-azabenzotriazol-1-yl)-N,N,N',N'-tetramethyluronium hexafluorophosphate (1.9 g, 5.0 mmol). The reaction mixture was stirred at room temperature for 2 hours and quenched with ice water (200 mL), extracted with EtOAc, washed with brine, dried with anhydrous Na$_2$SO$_4$, filtered and concentrated to give the crude product. The crude product was purified by silica gel chromatography eluted to give product REX-P-7 (1.2 g, 79.8%).

MS m/z [ESI]: 385.2 [M+1].

$^1$H-NMR (400 MHz, DMSO-d$_6$): δ=9.47 (t, J=6.0 Hz, 1H), 8.48-8.65 (m, 2H), 7.90-7.98 (m, 2H), 7.71 (s, 1H), 7.52-7.61 (m, 3H), 7.37-7.43 (m, 2H), 7.34 (d, J=4.8 Hz, 1H), 4.54 (d, J=6.0 Hz, 2H), 2.54 (s, 3H), 2.34 (s, 3H).

Example 7

N-((2',3-dimethyl-[2,4'-bipyridin]-5-yl)methyl)-1-methyl-5-phenyl-1H-pyrazole-3-carboxamide [REX-P-9]

Synthetic Routes:

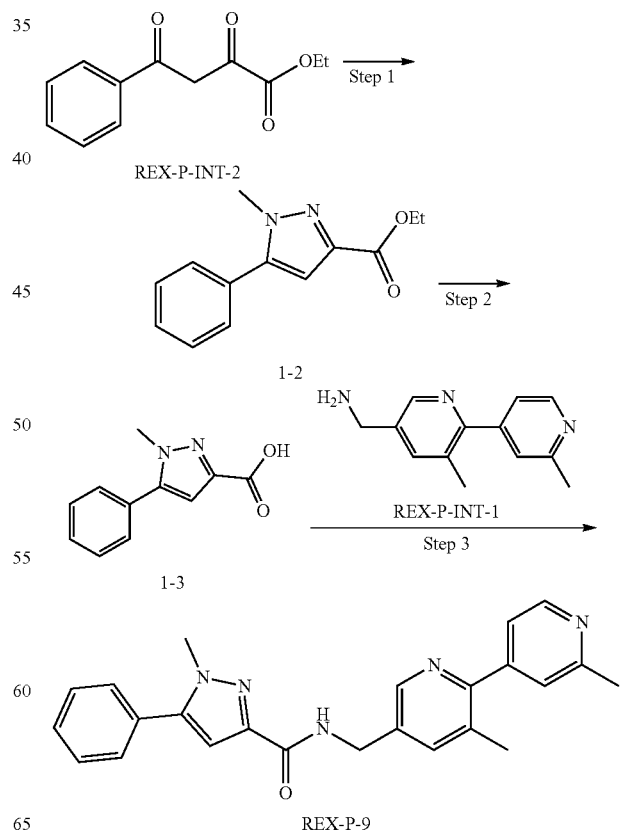

Step 1: Preparation of Compound 1-2

According to the reaction 2 in example 1 to give the intermediate compound REX-P-INT-2 1.0 g.

To a solution of REX-P-INT-2 (1.0 g, 4.5 mmol), methylhydrazine sulfate (1.0 g, 6.8 mmol) and NaOH (0.5 g, 13.6 mmol) in EtOH (50 mL). The reaction mixture was stirred at 70° C. overnight. The reaction mixture was quenched with ice water (100 mL), extracted with EtOAc, washed with brine, dried with anhydrous $Na_2SO_4$, filtered and concentrated to give the crude product. The crude product was purified by silica gel chromatography eluted to give product 1-2 (0.3 g, 28.7%).

MS m/z [ESI]: 231.1 [M+1].

Step 2: Preparation of Compound 1-3

To a solution of 1-2 (0.3 g, 1.3 mmol) in MeOH (5 mL) was added sodium hydroxide solution (10 mL, 4 M). The reaction mixture was stirred at room temperature for 2 hours and concentrated under reduced pressure to remove MeOH. The aqueous phase was acidified with aqueous HCl (1 M) till pH=3 and the mixture was extracted with EtOAc, dried with anhydrous $Na_2SO_4$, filtered and concentrated to give the crude product. The crude product was purified by silica gel chromatography eluted to give product 1-3 (242.7 m g, 92.4%).

MS m/z [ESI]: 203.1 [M+1].

Step 3: Preparation of Compound REX-P-9

According to the reaction 1 in example 1 to give the intermediate compound REX-P-INT-1 2.7 g.

To a solution of 1-3 (242.7 mg, 1.2 mmol) and REX-P-INT-1 (303.7 mg, 1.4 mmol) in DMSO (20 mL) was added N,N-diisopropylethylamine (0.6 mL, 3.6 mmol) and o-(7-azabenzotriazol-1-yl)-N,N,N',N'-tetramethyluronium hexafluorophosphate (527.3 mg, 1.4 mmol). The reaction mixture was stirred at room temperature for 2 hours and quenched with ice water (50 mL), extracted with EtOAc, washed with brine, dried with anhydrous $Na_2SO_4$, filtered and concentrated to give the crude product. The crude product was purified by silica gel chromatography eluted to give product REX-P-9 (361.8 mg, 75.9%).

MS m/z [ESI]: 398.2 [M+1].

$^1$H-NMR (400 MHz, DMSO-$d_6$): δ=9.17 (t, J=6.0 Hz, 1H), 8.51-8.54 (m, 2H), 7.75-7.79 (m, 2H), 7.71-7.73 (m, 1H), 7.40-7.47 (m, 3H), 7.31-7.36 (m, 3H), 4.53 (d, J=6.0 Hz, 2H), 4.12 (s, 3H), 2.54 (s, 3H), 2.35 (s, 3H).

Example 8

N-((2',3-dimethyl-[2,4'-bipyridin]-5-yl)methyl)-1-methyl-3-phenyl-1H-pyrazole-5-carboxamide [REX-P-1]

Synthetic Routes:

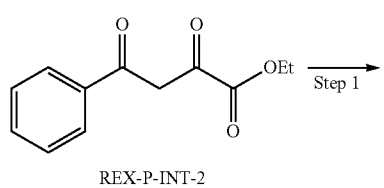

REX-P-INT-2

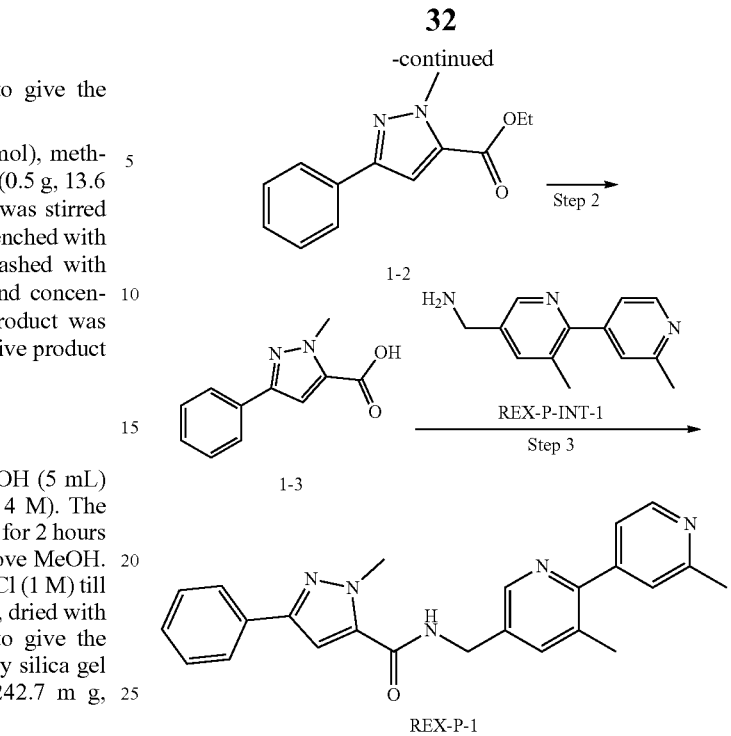

REX-P-1

Step 1: Preparation of Compound 1-2

According to the reaction 2 in example 1 to give the intermediate compound REX-P-INT-2 1.0 g.

To a solution of REX-P-INT-2 (1.0 g, 4.5 mmol), methylhydrazine sulfate (1.0 g, 6.8 mmol) and NaOH (0.5 g, 13.6 mmol) in EtOH (50 mL). The reaction mixture was stirred at 70° C. overnight. The reaction mixture was quenched with ice water (100 mL), extracted with EtOAc, washed with brine, dried with anhydrous $Na_2SO_4$, filtered and concentrated to give the crude product. The crude product was purified by silica gel chromatography eluted to give product 1-2 (247.5 mg, 23.9%).

MS m/z [ESI]: 231.1 [M+1].

Step 2: Preparation of Compound 1-3

To a solution of 1-2 (247.5 mg, 1.1 mmol) in MeOH (5 mL) was added sodium hydroxide solution (10 mL, 4 M). The reaction mixture was stirred at room temperature for 2 hours and concentrated under reduced pressure to remove MeOH. The aqueous phase was acidified with aqueous HCl (1 M) till pH=3 and the mixture was extracted with EtOAc, dried with anhydrous $Na_2SO_4$, filtered and concentrated to give the crude product. The crude product was purified by silica gel chromatography eluted to give product 1-3 (207.0 mg, 93.1%).

MS m/z [ESI]: 203.1 [M+1].

Step 3: Preparation of Compound REX-P-1

According to the reaction 1 in example 1 to give the intermediate compound REX-P-INT-1 2.7 g.

To a solution of 1-3 (207.0 mg, 1.0 mmol) and REX-P-INT-1 (260.3 mg, 1.2 mmol) in DMSO (20 mL) was added N,N-diisopropylethylamine (0.5 mL, 3.0 mmol) and o-(7-azabenzotriazol-1-yl)-N,N,N',N'-tetramethyluronium hexafluorophosphate (452.0 mg, 1.2 mmol). The reaction mixture was stirred at room temperature for 2 hours and quenched with ice water (50 mL), extracted with EtOAc, washed with brine, dried with anhydrous $Na_2SO_4$, filtered and to give the crude product. The crude product was purified by silica gel chromatography eluted to give product REX-P-9 (256.2 mg, 64.5%).

MS m/z [ESI]: 398.2 [M+1].

$^1$H-NMR (400 MHz, DMSO-d$_6$): δ=8.87 (t, J=6.0 Hz, 1H), 8.53 (d, J=5.2 Hz, 1H), 8.49 (s, 1H), 7.68 (s, 1H), 7.45-7.61 (m, 5H), 7.42 (s, 1H), 7.36 (d, J=4.8 Hz, 1H), 6.80 (s, 1H), 4.487 (d, J=6.0 Hz, 2H), 3.92 (s, 3H), 2.541 (s, 3H), 2.33 (s, 3H).

Example 9

N-((2',3-dimethyl-[2,4'-bipyridin]-5-yl)methyl)-5-phenyl-1,3,4-thiadiazole-2-carboxamide [REX-P-8]

Synthetic Routes:

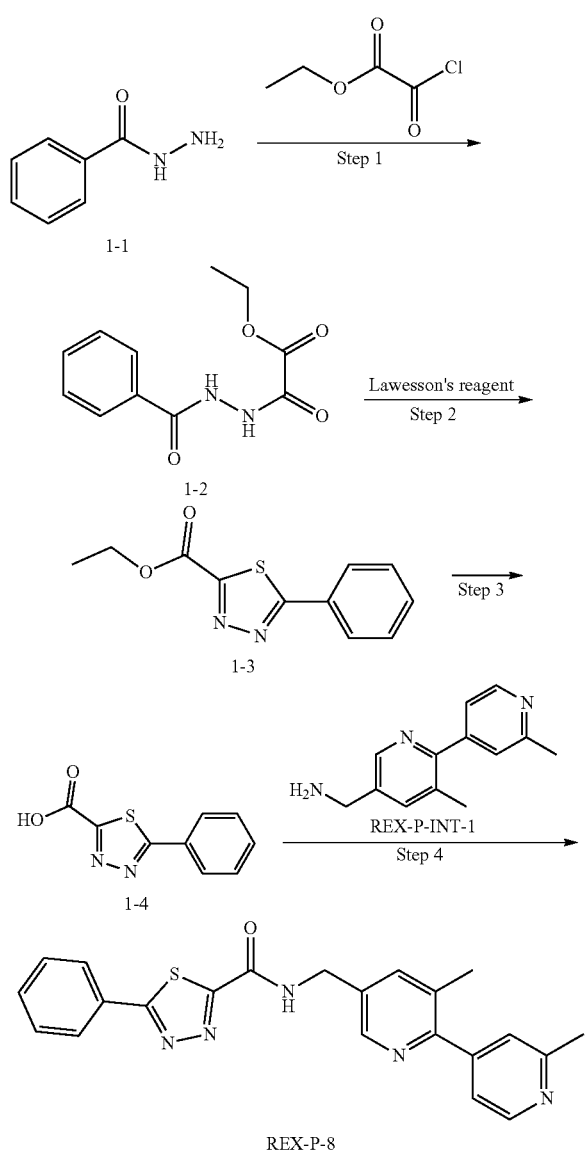

Step 1: Preparation of Compound 1-2

To a solution of 1-1 (2.0 g, 14.6 mmol) and Triethylamine (4 mL, 2.9 g, 29.3 mmol) in dichloromethane was added drop-wise ethyl oxalyl monochloride (2.0 g, 14.6 mmol). The reaction mixture was stirred at room temperature for 24 hours. The mixture was quenched with ice water (200 mL), extracted with dichloromethane, washed with brine, dried with anhydrous Na$_2$SO$_4$, filtered and concentrated to give the crude product. The crude product was purified by silica gel chromatography eluted to give product 1-2 (2.0 g, 57.6%).

MS m/z [ESI]: 237.1 [M+1].

Step 2: Preparation of Compound 1-3

To a solution of 1-2 (0.5 g, 2.1 mmol) and Lawesson's reagent (1.0 g, 2.5 mmol) in THF (50 mL). The reaction mixture was stirred at 70° C. over night. The mixture was quenched with ice water (100 mL), extracted with EtOAc, washed with brine, dried with anhydrous Na$_2$SO$_4$, filtered and concentrated to give the crude product. The crude product was purified by silica gel chromatography eluted to give product 1-3 (200 mg, 40.8%).

MS m/z [ESI]: 235.1 [M+1].

$^1$H-NMR (400 MHz, DMSO-d$_6$): δ=8.07-8.11 (m, 2H), 7.57-7.67 (m, 3H), 7.99 (s, 1H), 4.46 (q, J=7.2 Hz, 2H), 1.374 (t, J=7.2 Hz, 3H).

Step 3: Preparation of Compound 1-4

To a solution of 1-3 (150.0 mg, 0.6 mmol) in MeOH (10 mL) was added sodium hydroxide solution (2 mL, 1 M). The reaction mixture was stirred at room temperature for 2 hours and concentrated under reduced pressure to remove MeOH. The aqueous phase was acidified with aqueous HCl (1 M) till pH=3, filtered and dried under air to give the product 1-4 (120.0 m g, 90.8%).

MS m/z [ESI]: 207.0 [M+1].

Step 4: Preparation of Compound REX-P-8

According to the reaction 1 in example 1 to give the intermediate compound REX-P-INT-1 1.0 g.

To a solution of 1-4 (100.0 mg, 0.48 mmol) and REX-P-INT-1 (103.0 mg, 0.48 mmol) in DMSO (5 mL) was added N,N-diisopropylethylamine (188.0 mg, 1.4 mmol) and o-(7-azabenzotriazol-1-yl)-N,N,N',N'-tetramethyluronium hexafluorophosphate (203.0 mg, 0.53 mmol). The reaction mixture was stirred at room temperature for 2 hours and quenched with ice water (200 mL), extracted with EtOAc, dried with anhydrous Na$_2$SO$_4$, filtered and concentrated to give the crude product. The crude product was purified by silica gel chromatography eluted to give product REX-P-8 (45.0 mg, 23.0%).

MS m/z [ESI]: 402.1 [M+1].

$^1$H-NMR (400 MHz, DMSO-d$_6$): δ=9.93 (s, 1H), 8.50-8.55 (m, 2H), 8.06 (d, J=6.8 Hz, 2H), 7.73 (s, 1H), 7.56-7.66 (m, 3H), 7.40 (s, 1H), 7.34 (d, J=4.4 Hz, 1H), 4.56 (d, J=4 Hz, 2H), 2.53 (s, 3H), 2.33 (s, 3H).

Example 10

5-(4-chlorophenyl)-N-((2',3-dimethyl-[2,4'-bipyridin]-5-yl)methyl)thiazole-2-carboxamide [REX-P-13]

Synthetic Routes:

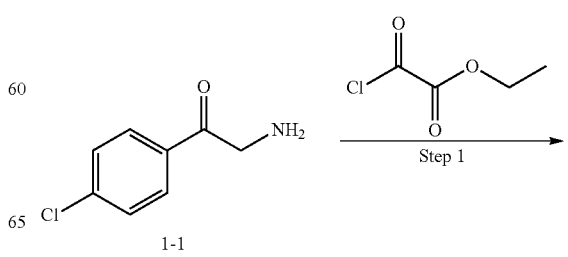

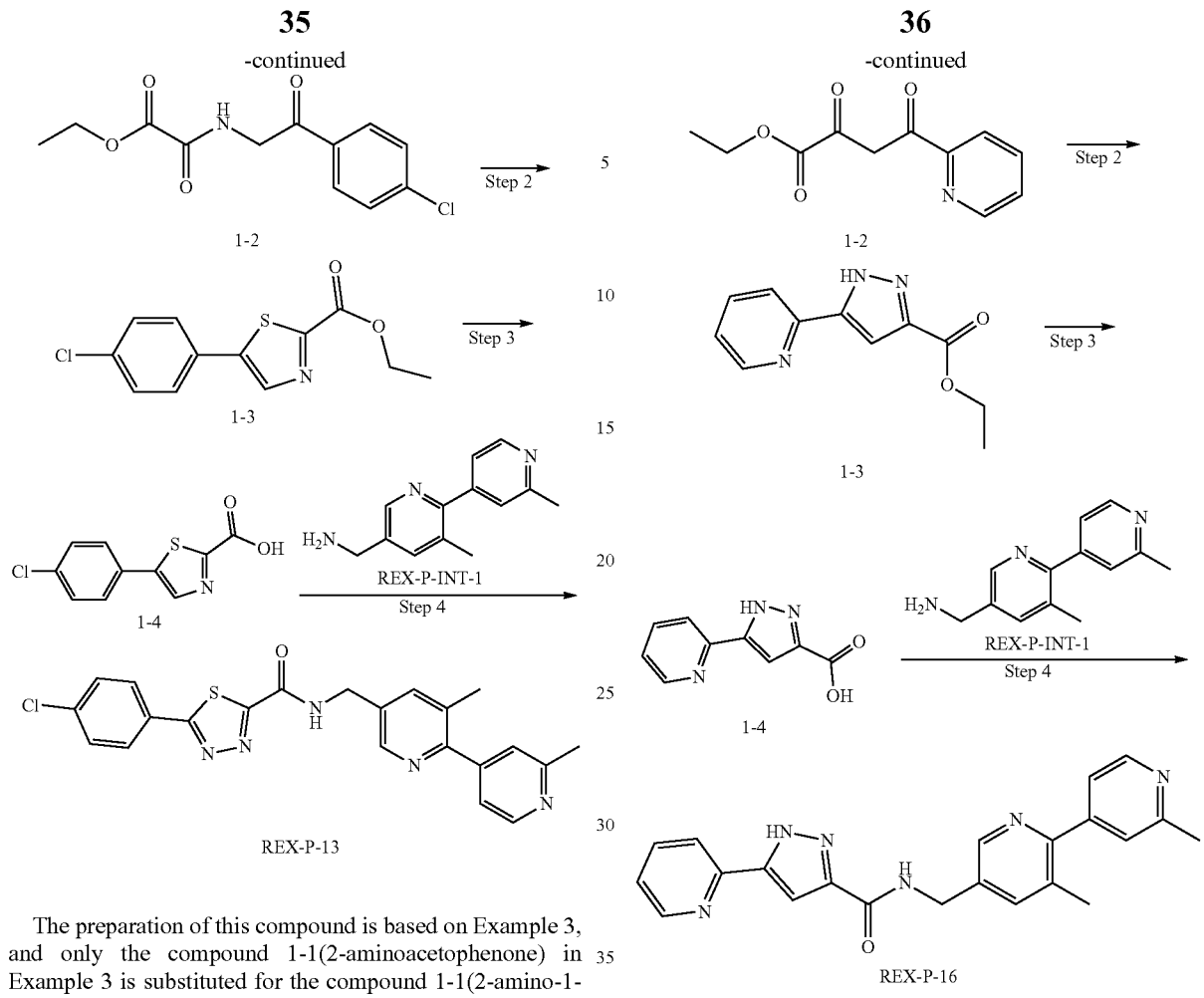

The preparation of this compound is based on Example 3, and only the compound 1-1(2-aminoacetophenone) in Example 3 is substituted for the compound 1-1(2-amino-1-(4-chlorophenyl)ethanone) in Example 10. The other methods are the same to give the final compound REX-P-13 (120.5 mg, 25.2%).

MS m/z [ESI]: 435.9 [M+1].

$^1$H-NMR (400 MHz, DMSO-d$_6$): δ=9.55 (t, J=6.0 Hz, 1H), 8.47-8.49 (m, 2H), 7.78-7.80 (m, 2H), 7.67 (s, 1H), 7.51-7.52 (m, 2H), 7.37 (s, 1H), 7.30-7.31 (m, 1H), 4.51 (d, J=6 Hz, 2H), 2.52 (s, 3H), 2.32 (s, 3H).

Example 11

N-((2',3-dimethyl-[2,4'-bipyridin]-5-yl)methyl)-5-(pyridin-2-yl)-1H-pyrazole-3-carboxamide [REX-P-16]

Synthetic Routes:

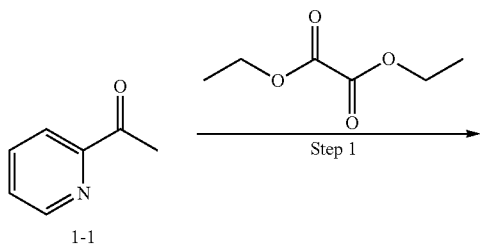

The preparation of this compound is based on synthesis scheme 2 in Example 1, and only the compound 1-1 (acetophenone) in Example 1 is substituted for the compound 1-1 (2-acetylpyridine) in Example 11. The other methods are the same to give the final compound REX-P-16 (150.0 mg, 30.2%).

MS m/z [ESI]: 385.3 [M+1].

$^1$H-NMR (400 MHz, DMSO-d$_6$): δ=13.93 (q, 1H), 8.99 (t, J=6.0 Hz, 1H), 8.60 (s, 1H), 8.46-8.49 (m, 2H), 7.87-7.92 (m, 2H), 7.67 (s, 1H), 7.31-7.38 (m, 3H), 4.49 (d, J=6 Hz, 2H), 2.52 (s, 3H), 2.32 (s, 3H).

Example 13

2-(3-chlorophenyl)-N-((2',3-dimethyl-[2,4'-bipyridin]-5-yl)methyl)thiazole-5-carboxamide [REX-P-22]

Synthetic Routes:

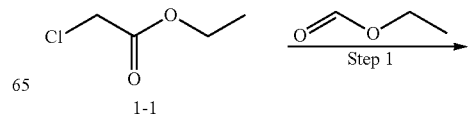

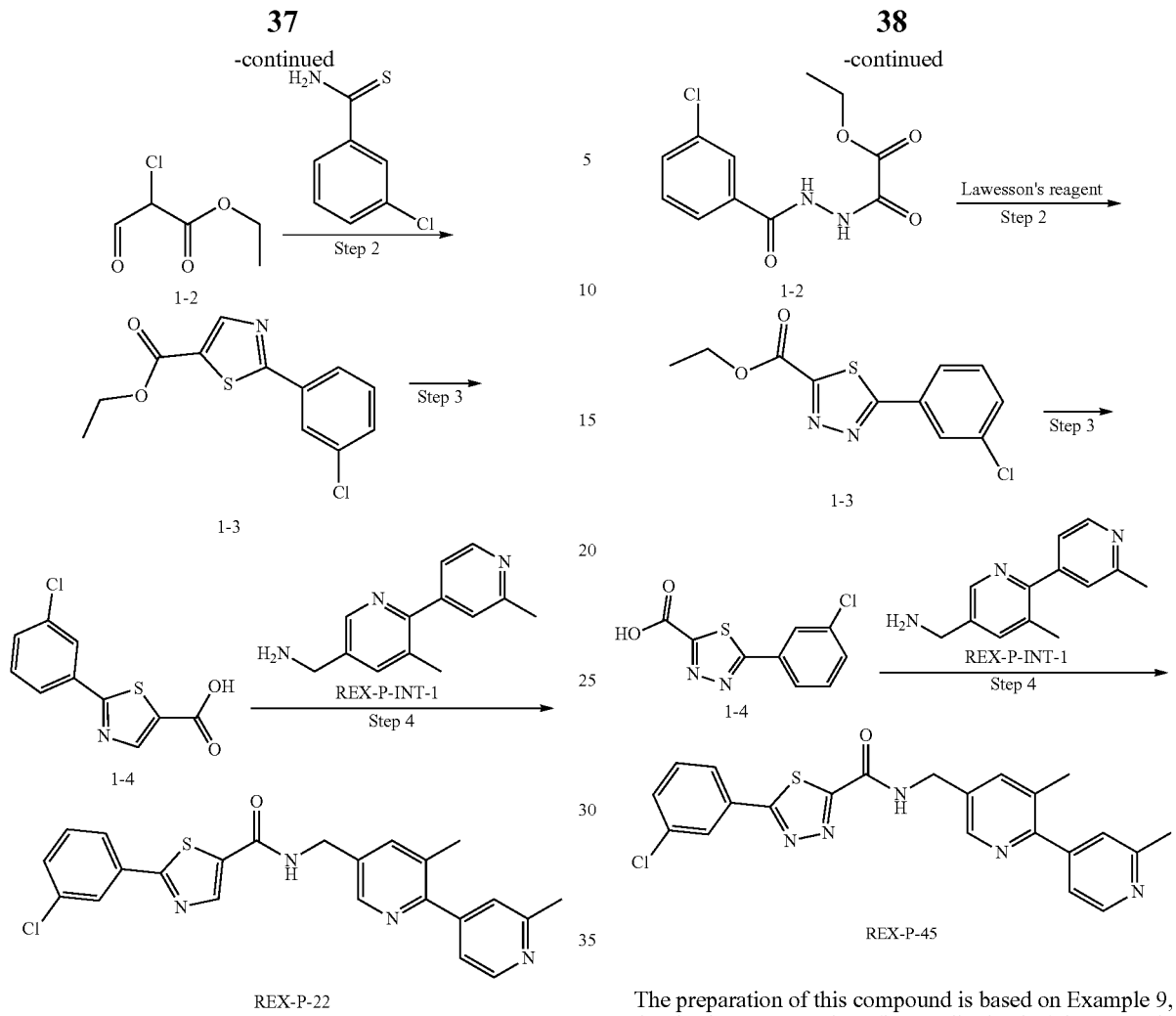

The preparation of this compound is based on Example 2, and only the compound thiobenzamide of step 2 in Example 2 is substituted for the compound 3-chlorobenzenecarbothioamide in Example 13. The other methods are the same to give the final compound REX-P-22 (100.0 mg, 20.3%).

MS m/z [ESI]: 401.5 [M+1].

$^1$H-NMR (400 MHz, DMSO-$d_6$): δ=9.45 (s, 1H), 8.53 (s, 3H), 7.90-8.08 (m, 2H), 7.48-7.81 (m, 3H), 7.31-7.45 (m, 2H), 4.53 (d, J=6 Hz, 2H), 2.33 (s, 3H), 1.25 (s, 3H).

Example 14

5-(3-chlorophenyl)-N-((2',3-dimethyl-[2,4'-bipyridin]-5-yl)methyl)-1,3,4-thiadiazole-2-carboxamide [REX-P-45]

Synthetic Routes:

The preparation of this compound is based on Example 9, and only the compound 1-1(benzoylhydrazine) in Example 9 is substituted for the compound 1-1(3-chlorobenzhydrazide) in Example 14. The other methods are the same to give the final compound REX-P-45 (200.0 mg, 35.4%).

MS m/z [ESI]: 436.3 [M+1].

$^1$H-NMR (400 MHz, DMSO-$d_6$): δ=10.00 (t, J=6.0 Hz, 1H), 8.53-8.55 (m, 2H), 8.13-8.14 (m, 2H), 8.04 (d, J=6.8 Hz, 2H), 7.72-7.75 (m, 2H), 7.62-7.65 (m, 1H), 7.43 (s, 1H), 7.37-7.38 (m, 1H), 4.56 (d, J=4 Hz, 2H), 2.54 (s, 3H), 2.34 (s, 3H).

Example 15

N-((2',3-dimethyl-[2,4'-bipyridin]-5-yl)methyl)-5-(3-fluorophenyl)-1,3,4-thiadiazole-2-carboxamide [REX-P-46]

Synthetic Routes:

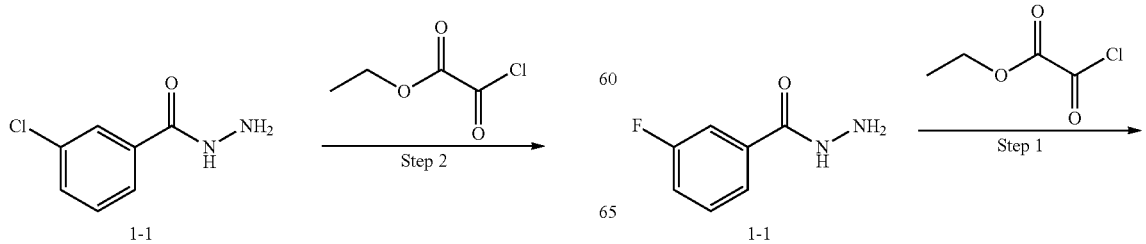

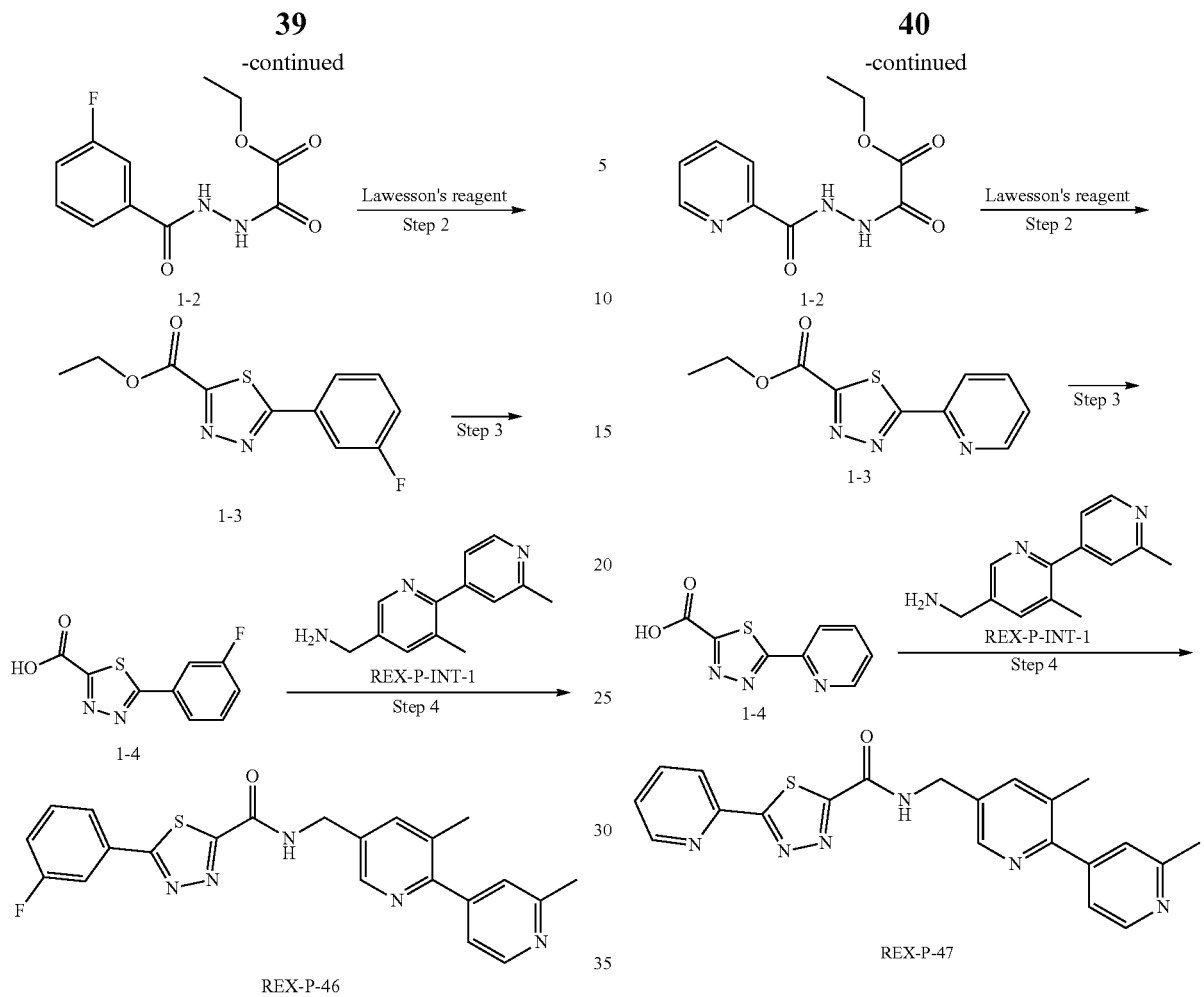

The preparation of this compound is based on Example 9, and only the compound 1-1(benzoylhydrazine) in Example 9 is substituted for the compound 1-1(3-Fluorobenzoic hydrazide) in Example 15. The other methods are the same to give the final compound REX-P-46 (210.0 mg, 35.8%).

MS m/z [ESI]: 420.4 [M+1].

$^1$H-NMR (400 MHz, CDCl$_3$): δ=8.57-8.59 (m, 2H), 7.94 (s, 1H), 7.74-7.77 (m, 2H), 7.66 (s, 1H), 7.46-7.56 (m, 1H), 7.33 (s, 1H), 7.25-7.27 (m, 2H), 4.74 (d, J=4 Hz, 2H), 2.63 (s, 3H), 2.37 (s, 3H).

Example 16

N-((2',3-dimethyl-[2,4'-bipyridin]-5-yl)methyl)-5-(pyridin-2-yl)-1,3,4-thiadiazole-2-carboxamide [REX-P-47]

Synthetic Routes:

The preparation of this compound is based on Example 9, and only the compound 1-1(benzoylhydrazine) in Example 9 is substituted for the compound 1-1(2-pyridinecarboxyli-cacid) in the Example 16. The other methods are the same to give the final compound REX-P-47 (150.0 mg, 25.8%).

MS m/z [ESI]: 403.4 [M+1].

$^1$H-NMR (400 MHz, CDCl$_3$): δ=8.63 (t, J=6.0 Hz, 1H), 8.52-8.57 (m, 2H), 8.24-8.28 (m, 2H), 7.82 (s, 1H), 7.63 (s, 1H), 7.26-7.27 (m, 1H), 7.19-7.20 (m, 1H), 4.70 (d, J=4 Hz, 2H), 2.57 (s, 3H), 2.30 (s, 3H).

Example 17

N-((2',3-dimethyl-[2,4'-bipyridin]-5-yl)methyl)-5-(5-fluoropyridin-3-yl)-1,3,4-thiadiazole-2-carboxamide [REX-P-49]

Synthetic Routes:

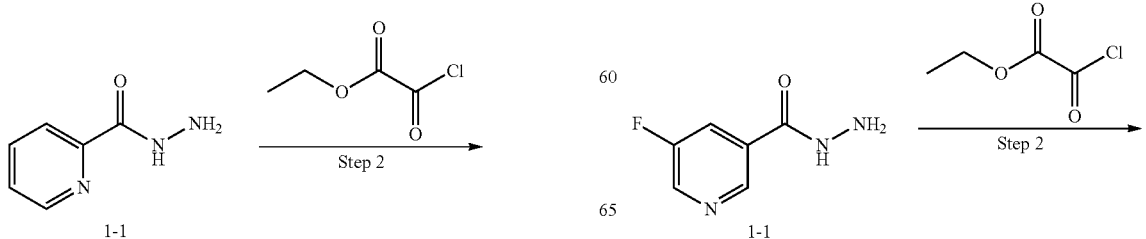

-continued

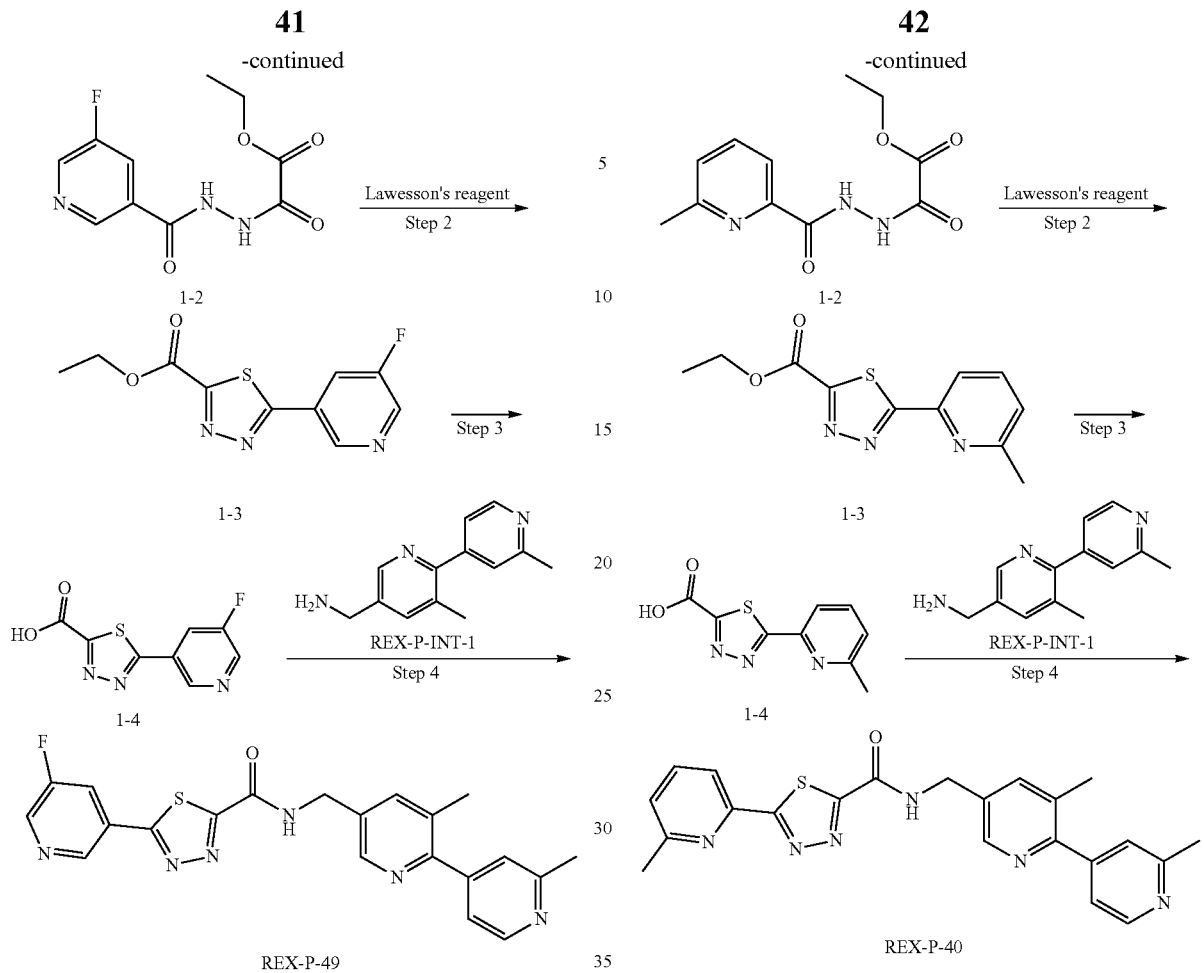

REX-P-49

REX-P-40

The preparation of this compound is based on Example 9, and only the compound 1-1(benzoylhydrazine) in Example 9 is substituted for the compound 1-1(5-fluoropyridine-3-carbohydrazide) in Example 17. The other methods are the same to give the final compound REX-P-49 (100.0 mg, 18.8%).

MS m/z [ESI]: 420.9 [M+1].

$^1$H-NMR (400 MHz, DMSO-$d_6$): δ=9.96 (t, J=6.0 Hz, 1H), 9.06 (s, 1H), 8.76 (s, 1H), 8.35-8.44 (m, 2H), 7.66 (s, 1H), 7.27-7.34 (m, 1H), 4.50 (d, J=4 Hz, 2H), 2.45 (s, 3H), 2.26 (s, 3H).

The preparation of this compound is based on Example 9, and only the compound 1-1(benzoylhydrazine) in Example 9 is substituted for the compound 1-1(6-methylpicolinohydrazide) in Example 18. The other methods are the same to give the final compound REX-P-50 (110.0 mg, 20.3%).

MS m/z [ESI]: 417.0 [M+1].

$^1$H-NMR (400 MHz, DMSO-$d_6$): δ=9.97 (t, J=6.0 Hz, 1H), 8.52-8.53 (m, 1H), 8.13-8.14 (m, 1H), 7.93-7.95 (m, 1H), 7.74 (s, 1H), 7.49-7.51 (m, 1H), 7.41 (s, 1H), 7.34-7.35 (m, 1H), 4.56 (d, J=4 Hz, 2H), 2.57 (s, 3H), 2.53 (s, 3H), 2.34 (s, 3H).

Example 18

N-((2',3-dimethyl-[2,4'-bipyridin]-5-yl)methyl)-5-(6-methylpyridin-2-yl)-1,3,4-thiadiazole-2-carboxamide [REX-P-50]

Synthetic Routes:

Example 19

N-((2',3-dimethyl-[2,4'-bipyridin]-5-yl)methyl)-5-(pyrazin-2-yl)-1,3,4-thiadiazole-2-carboxamide [REX-P-52]

Synthetic Routes:

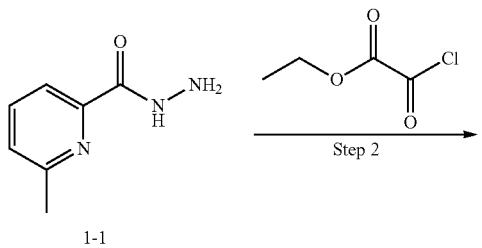

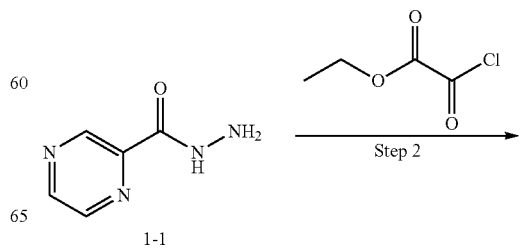

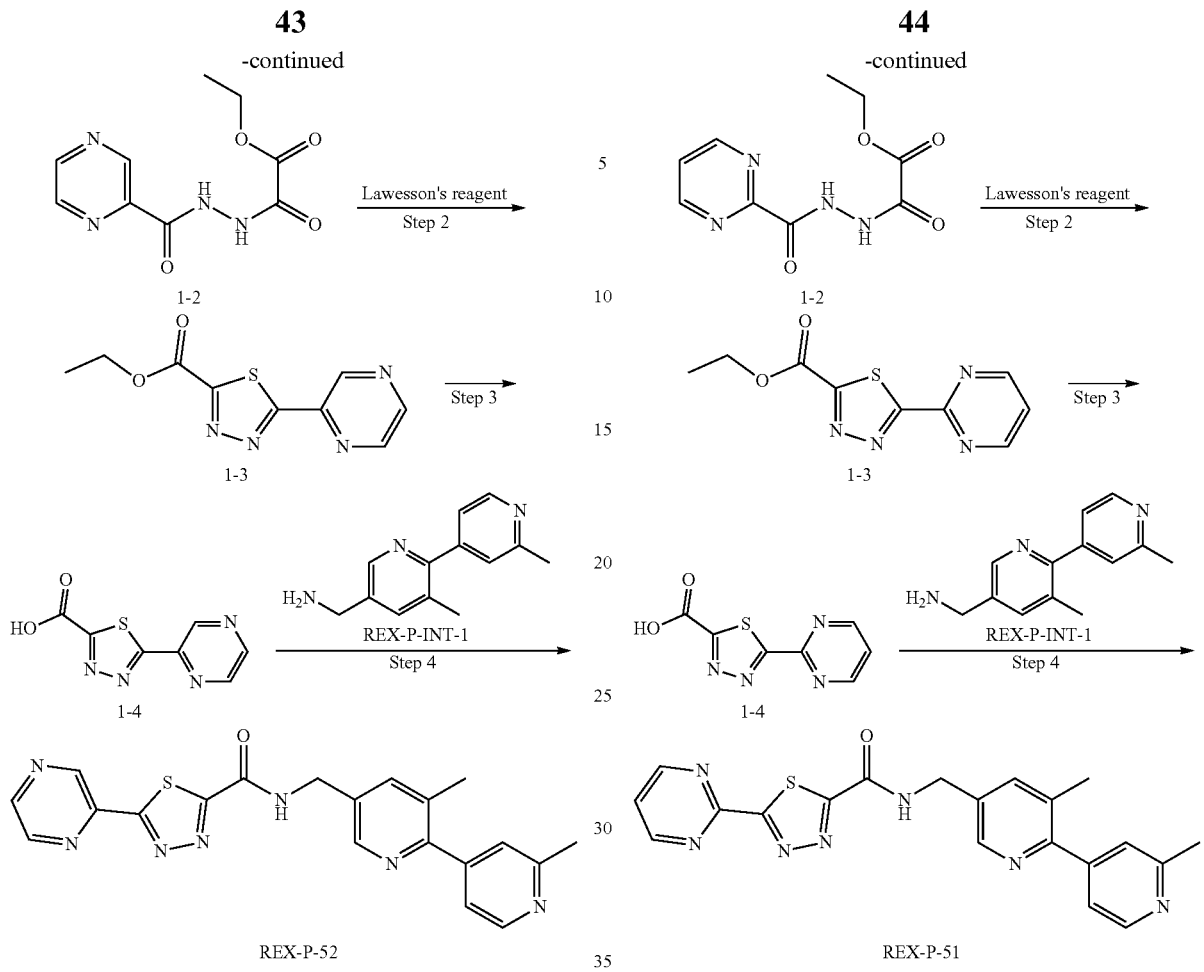

The preparation of this compound is based on Example 9, and only the compound 1-1(benzoylhydrazine) in Example 9 is substituted for the compound 1-1(pyrazine-2-carbohydrazide) in Example 19. The other methods are the same to give the final compound REX-P-52 (140.0 mg, 23.2%).

MS m/z [ESI]: 404.0 [M+1].

$^1$H-NMR (400 MHz, DMSO-d$_6$): δ=9.48 (s, 1H), 8.66 (s, 1H), 8.59 (s, 1H), 8.48-8.49 (m, 2H), 8.33-8.34 (m, 1H), 7.60 (s, 1H), 7.23-7.25 (m, 1H), 7.16-7.18 (m, 1H), 4.67 (d, J=4 Hz, 2H), 2.54 (s, 3H), 2.29 (s, 3H).

Example 20

N-((2',3-dimethyl-[2,4'-bipyridin]-5-yl)methyl)-5-(pyrimidin-2-yl)-1,3,4-thiadiazole-2-carboxamide [REX-P-51]

Synthetic Routes:

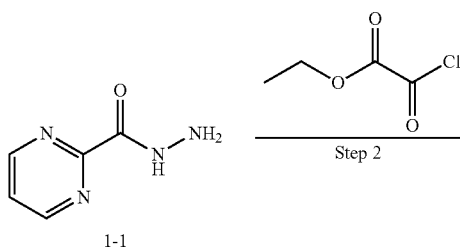

The preparation of this compound is based on Example 9, and only the compound 1-1(benzoylhydrazine) in Example 9 is substituted for the compound 1-1(pyrimidine-2-carbohydrazide) in Example 20. The other methods are the same to give the final compound REX-P-51 (100.0 mg, 18.2%).

MS m/z [ESI]: 404.0 [M+1].

$^1$H-NMR (400 MHz, DMSO-d$_6$): δ=9.98 (d, 2H), 8.51 (d, 1H), 7.85 (s, 1H), 7.61-7.64 (m, 1H), 7.42 (s, 1H), 7.35-7.36 (m, 2H), 4.68 (d, J=4 Hz, 2H), 2.59 (s, 3H), 2.35 (s, 3H).

Example 21

N-((2',3-dimethyl-[2,4'-bipyridin]-5-yl)methyl)-5-(3-fluoropyridin-2-yl)-1,3,4-thiadiazole-2-carboxamide [REX-P-48]

Synthetic Routes:

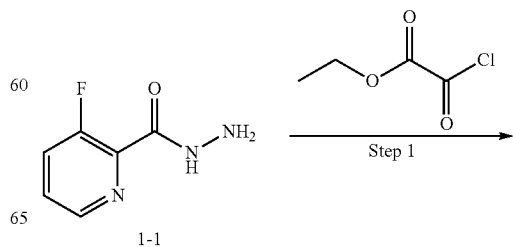

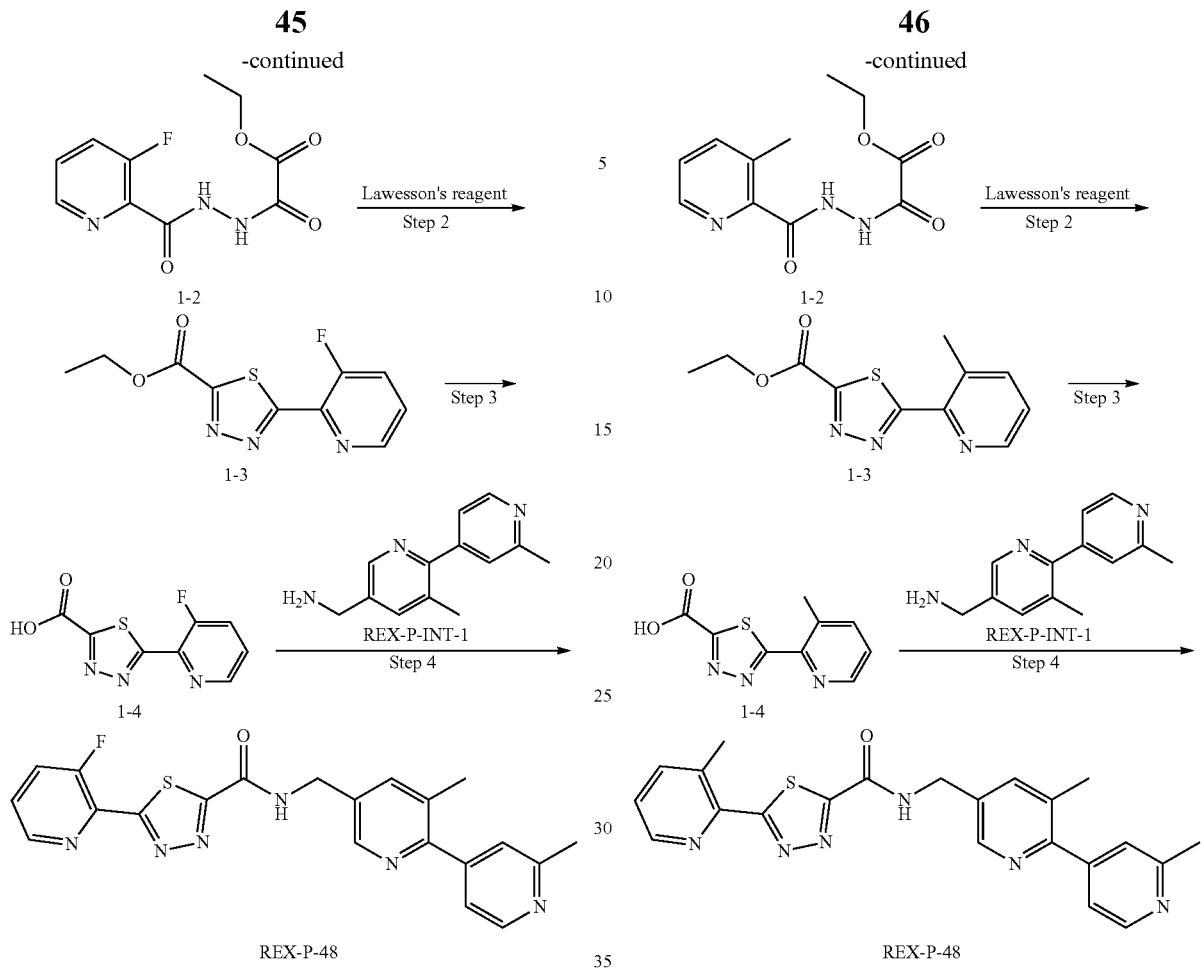

The preparation of this compound is based on Example 9, and only the compound 1-1(benzoylhydrazine) in Example 9 is substituted for the compound 1-1(3-fluoropicolinohydrazide) in Example 21. The other methods are the same to give the final compound REX-P-48 (150.0 mg, 28.2%).

MS m/z [ESI]: 421.0 [M+1].

$^1$H-NMR (400 MHz, DMSO-d$_6$): δ=8.52-8.58 (m, 3H), 7.87-7.88 (m, 2H), 7.64-7.68 (m, 1H), 7.44 (s, 1H), 7.36-7.37 (m, 2H), 4.69 (d, J=4 Hz, 2H), 2.60 (s, 3H), 2.36 (s, 3H).

Example 22

N-((2',3-dimethyl-[2,4'-bipyridin]-5-yl)methyl)-5-(3-methylpyridin-2-yl)-1,3,4-thiadiazole-2-carboxamide [REX-P-56]

Synthetic Routes:

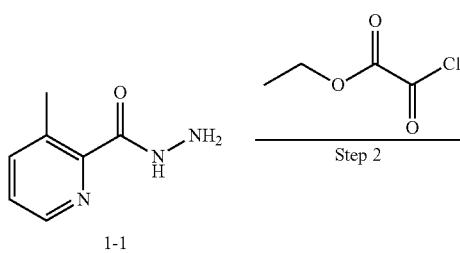

The preparation of this compound is based on Example 9, and only the compound 1-1(benzoylhydrazine) in Example 9 is substituted for the compound 1-1(3-methylpicolinohydrazide) in Example 22. The other methods are the same to give the final compound REX-P-56 (150.0 mg, 26.2%).

MS m/z [ESI]: 417.0 [M+1].

$^1$H-NMR (400 MHz, DMSO-d$_6$): δ=9.89 (s, 1H), 8.46 (s, 2H), 8.06-8.07 (m, 1H), 7.68-7.69 (m, 1H), 7.44 (s, 1H), 7.29-7.35 (m, 3H), 4.50 (d, J=4 Hz, 2H), 2.50 (s, 3H), 2.47 (s, 3H), 2.29 (s, 3H).

Example 23

N-((2',3-dimethyl-[2,4'-bipyridin]-5-yl)methyl)-5-(4-methylpyridin-3-yl)-1,3,4-thiadiazole-2-carboxamide [REX-P-55]

Synthetic Routes:

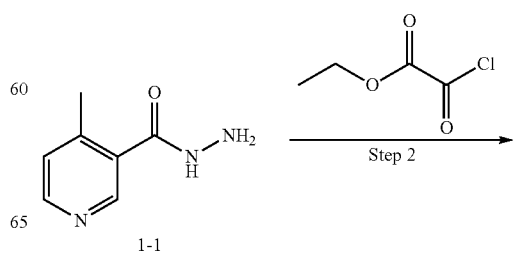

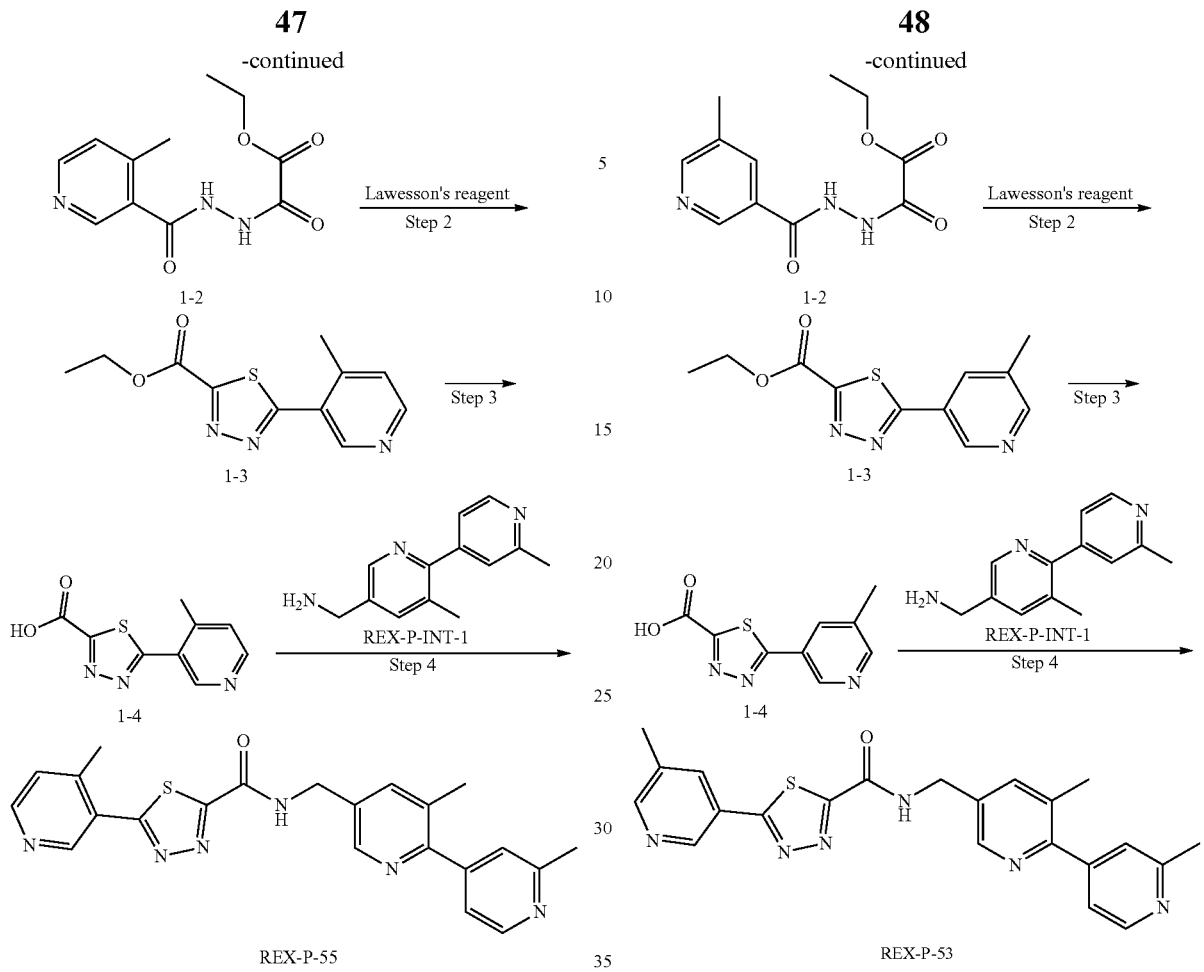

The preparation of this compound is based on Example 9, and only the compound 1-1(benzoylhydrazine) in Example 9 is substituted for the compound 1-1(4-methylnicotinohydrazide) in Example 23. The other methods are the same to give the final compound REX-P-55 (100.0 mg, 20.2%).

MS m/z [ESI]: 417.0 [M+1].

$^1$H-NMR (400 MHz, DMSO-d$_6$): δ=9.95 (s, 1H), 8.84 (s, 1H), 8.46-8.54 (m, 3H), 7.67 (s, 1H), 7.31-7.43 (m, 3H), 4.50 (d, J=4 Hz, 2H), 2.50 (s, 3H), 2.47 (s, 3H), 2.29 (s, 3H).

Example 24

N-((2',3-dimethyl-[2,4'-bipyridin]-5-yl)methyl)-5-(5-methylpyridin-3-yl)-1,3,4-thiadiazole-2-carboxamide [REX-P-53]

Synthetic Routes:

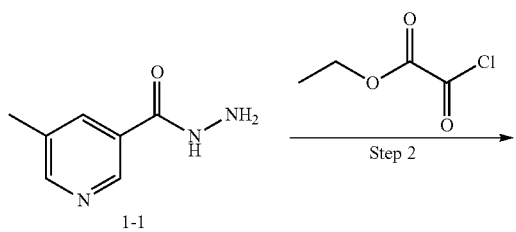

The preparation of this compound is based on Example 9, and only the compound 1-1(benzoylhydrazine) in Example 9 is substituted for the compound 1-1(5-methylnicotinohydrazide) in Example 24. The other methods are the same to give the final compound REX-P-53 (120.0 mg, 22.5%).

MS m/z [ESI]: 417.0 [M+1].

$^1$H-NMR (400 MHz, DMSO-d$_6$): δ=9.97 (s, 1H), 8.99 (s, 1H), 8.47-8.59 (m, 3H), 8.24 (s, 1H), 7.69 (s, 1H), 7.29-7.36 (m, 2H), 4.50 (d, J=4 Hz, 2H), 2.47 (s, 3H), 2.37 (s, 3H), 2.29 (s, 3H).

Example 25 Zebrafish Phenotype Screening Assay

Zebrafish *Danio rerio* is emerging as a predictive vertebrate animal model for in vivo assessment of drug efficacy, toxicity, and safety. An important advantage of the zebrafish animal model is that the morphological and molecular basis of tissues and organs is either identical or similar to other vertebrates, including humans. The sequence and presumed function of many genes that are important for vertebrates are conserved in the zebrafish, homology is as high as 85%. Wnt's are secreted proteins that are critical for normal embryonic development and homeostasis of select adult tissues. Wnt signaling regulates diverse developmental and homeostatic functions, including proliferation, differentiation, cell polarity, motility, and migration (Wolfram Goessling, Trista E. North, Sabine Loewer, et al. (2009). Genetic Interaction of PGE2 and Wnt Signaling Regulates Developmental Specification of Stem Cells and Regeneration. Cell, 136(6): 1136-1147.). Pathological states that may arise from altered stem cell function, such as degenerative diseases and cancer, are frequently associated with changes in Wnt/β-catenin pathway activity. Notably, 90% of colorectal cancers harbor loss-of-function mutations in the adenomatosis polyposis *coli* gene (APC), a major suppressor of the Wnt/β-catenin pathway (Hans Clevers, Roel Nusse. (2012). Wnt/β-Catenin Signaling and Disease. Cell, 149(6): 1192-1205.).

Wnt signaling is involved in virtually every aspect of embryonic development and also controls homeostatic self-renewal in a number of adult tissues. Therefore, we investigate the effect of compounds on zebrafish axis formation and regeneration of tailfin resected, taking advantage of the conservation in Wnt pathway of different species, and the superiority of zebrafish phenotype. In this assay, response the activity of inhibiting the Wnt pathway.

Experiment (1): The Effect of Compounds on Axis Formation of Zebrafish

Method: Zebrafish embryos were collected after natural spawning. Embryos were treated from the 16 cell stage (3 hours post fertilization) with different concentration series 100 μM~0.001 μM of the compound in 1% DMSO/fish water or with DMSO equivalent. The zebrafish were placed in a 6-well microplate at a density of 20 zebrafish per well with 3 mL of fish water. Zebrafish were incubated at 28.5° C. in the dark until 48 h post fertilization, then anesthetized, and imaged under a dissecting stereomicroscope installed with a high-speed video camera (JVC, Japan). Quantitative length of axis was performed with NIS-Elements D 3.1 soft and pixels data were expressed as mean±SEM. The effect of compound on axis formation of zebrafish was calculated based on the following formula:

Inhibition on axis growth (%)=[1−Pixel(compound)/Pixel(vehicle)]×100%

Inhibition curves were generated using GraphPad Prism 6.0 (GraphPad Software Inc., San Diego Calif.) and $IC_{50}$ was determined with logistic regression.

Figure 2:
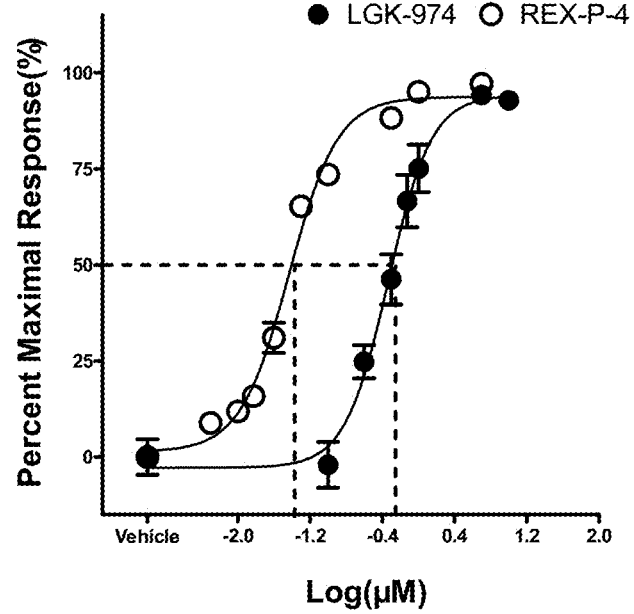
FIG. 2 is a graph showing the dose-response relationship for the growth inhibition of the axis formation of AB type zebrafish after 48 h treatment (mean±sd)

Results: $IC_{50}$ of the compounds on axis formation of zebrafish is listed in Table 1; Presentative images of axis formation of zebrafish by the compound are shown in FIG. 1; The dose-response curves are shown in FIG. 2.

TABLE 1

Inhibition activity of compounds on axis formation of zebrafish

| Compounds | $IC_{50}$ (μM) |
|---|---|
| LGK-974 | 0.583 |
| REX-P-2 | 8.233 |
| REX-P-16 | >10 |
| REX-P-9 | >20 |
| REX-P-1 | 29.88 |
| REX-P-3 | 0.144 |
| REX-P-22 | 0.178 |
| REX-P-4 | 0.0369 |
| REX-P-12 | >100 |
| REX-P-13 | >10 |
| REX-P-8 | 0.021 |
| REX-P-45 | 0.014 |
| REX-P-46 | 0.01 |
| REX-P-47 | 0.163 |
| REX-P-48 | 0.896 |
| REX-P-49 | 0.052 |
| REX-P-50 | 0.064 |
| REX-P-51 | >10 |
| REX-P-52 | 0.64 |
| REX-P-56 | 0.062 |

TABLE 1-continued

Inhibition activity of compounds on axis formation of zebrafish

| Compounds | $IC_{50}$ (μM) |
|---|---|
| REX-P-5 | >40 |
| REX-P-6 | >100 |
| REX-P-7 | 0.024 |

Note:
$IC_{50}$ is defined as the concentration at which 50% of axis formation is inhibited.

Some compounds in Table 1 were selected to further evaluate the effect on tailfin regeneration of zebrafish.

Experiment (2): The Effect of Compounds on Tailfin Regeneration of Zebrafish

Method: Three days post fertilization (d.p.f) zebrafish with resected caudal fins were placed in water containing 1% DMSO carrier or compounds (10 μM~0.001 μM) until 7 d.p.f. The zebrafish were placed in a 6-well microplate at a density of 15 zebrafish per well with 3 mL of fish water. Zebrafish were incubated at 28.5° C. in the dark until 7 d.p.f., then anesthetized, and imaged under a dissecting stereomicroscope installed with a high-speed video camera (JVC, Japan). Quantitative length of regeneration of tailfin was performed and pixels data were expressed as mean±SEM. The effect of compound on regeneration of tailfin of zebrafish was calculated based on the following formula:

Drug inhibition on regeneration of tailfin (%)=[1−Pixel(compound)/Pixel(vehicle)]×100%.

Inhibition curves were generated using GraphPad Prism 6.0 (GraphPad Software Inc., San Diego Calif.) and $IC_{50}$ was determined with logistic regression.

Figure 3:
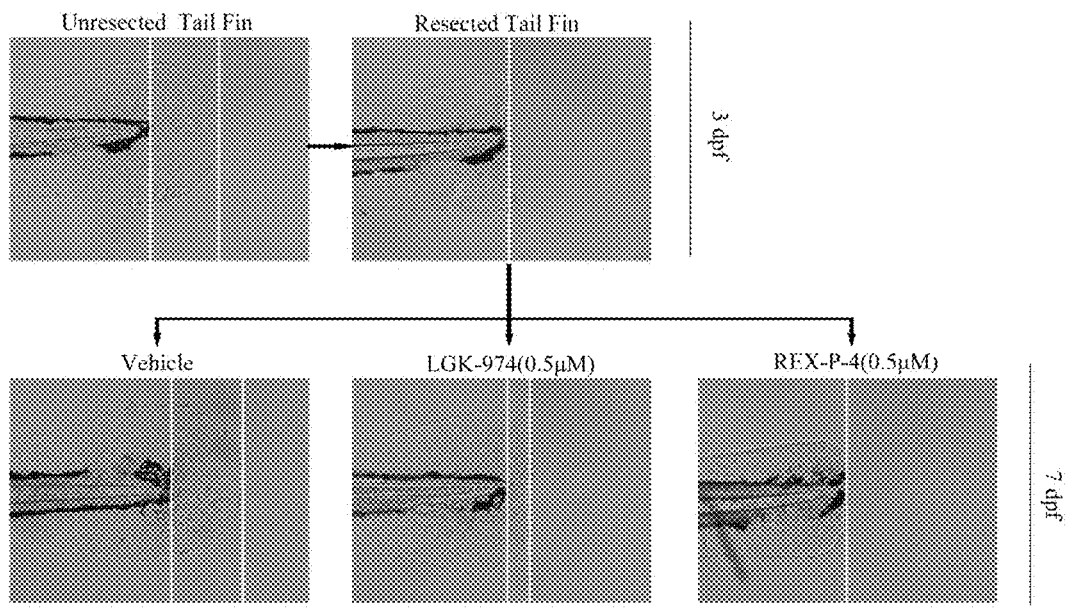
FIG. 3 is a diagram showing the resected-rail regeneration inhibition of AB type zebrafish after 7dpf treatment
Figure 4:
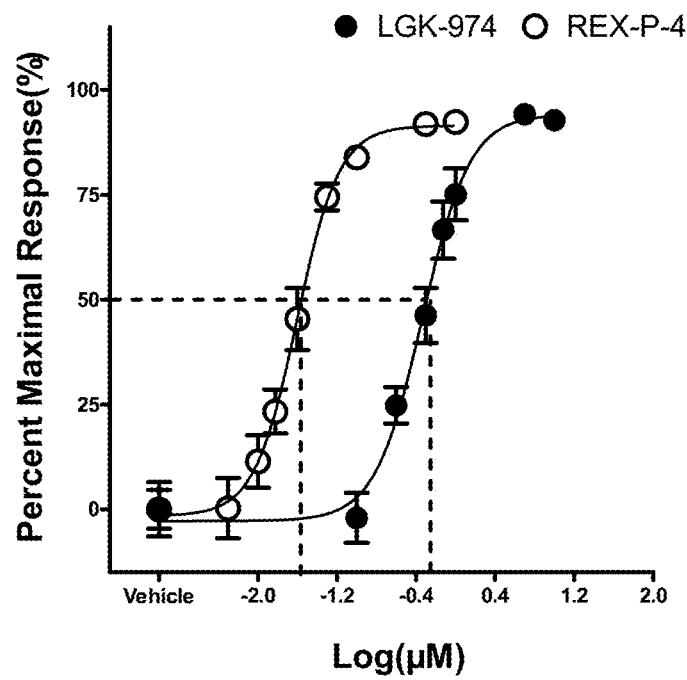
FIG. 4 is a graph showing the dose-response relationship for the resected-tail regeneration inhibition of AB type zebrafish after 7dpf treatment (mean±sd)

Results: $IC_{50}$ of compounds in regeneration of zebrafish tailfin is listed in following Table 2; REX-P-4 inhibition regeneration of zebrafish tailfin is shown in FIG. 3; The dose-response figure is shown in FIG. 4.

TABLE 2

Inhibition activity of compound on regeneration of zebrafish tailfin resected

| Compounds | $IC_{50}$ (μM) |
|---|---|
| LGK-974 | 0.462 |
| REX-P-2 | 3.908 |
| REX-P-3 | 0.084 |
| REX-P-22 | 0.028 |
| REX-P-8 | 0.027 |
| REX-P-45 | 0.023 |
| REX-P-46 | 0.016 |
| REX-P-47 | 0.207 |
| REX-P-48 | 0.721 |
| REX-P-49 | 0.137 |
| REX-P-50 | 0.111 |
| REX-P-52 | 0.746 |
| REX-P-7 | 0.047 |

Example 26 293 T/TOPLUC-Wnt3a Luciferase Report Gene Assay

In this assay, HEK293 cells harboring a luciferase-based Wnt/β-catenin reporter (Super 8×TOPFLASH) were cocultured with L-Wnt3a-expressing cells. 293T/TOPLUC-Wnt3a were incubated with small molecules for 24 h. The level of the Luciferase reporter gene was used as an indicator for Wnt ligand-driven, LEF/TCF-dependent transcriptional activities. $IC_{50}$ is defined as the compound concentration at which 50% of luciferase reporter activity is inhibited.

Results: REX-P compounds were investigated on Crown-Bio Cell plateform to assay the activity of inhibiting Wnt/β-catenin reporter activity, results are shown in Table 3. The results show that all compounds potently inhibit Wnt signaling in vitro.

TABLE 3

Activity assay of compound on inhibiting Wnt/β-catenin reporter gene readout

| Compounds | IC50 (nM) |
| --- | --- |
| LGK-974 | 0.574 |
| REX-P-2 | 1.76 |
| REX-P-16 | 16.756 |
| REX-P-9 | >1000 |
| REX-P-1 | 92.58 |
| REX-P-3 | <0.1 |
| REX-P-22 | 0.72 |
| REX-P-4 | <0.1 |
| REX-P-12 | 9.16 |
| REX-P-13 | >1000 |
| REX-P-8 | 1.92 |
| REX-P-45 | 0.31 |
| REX-P-46 | 0.125 |
| REX-P-47 | 0.673 |
| REX-P-49 | 0.248 |
| REX-P-50 | 0.389 |
| REX-P-52 | 1.384 |
| REX-P-5 | >1000 |
| REX-P-6 | >1000 |
| REX-P-7 | 0.69 |

Example 27 Metabolic Stability and In Vivo PK Assay

Metabolic stability and pharmacokinetic characteristics of REX-P-7 were detected in human and mouse liver microsomes and in Balb/c mice, respectively.

Method of PK experiment: 18 male Balb/c mice were divided into 2 groups, 9 animals in each group. Group 1 was administered intravenously with REX-P-7 at a dose of 5 mg/kg. Group 2 was administered orally with REX-P-7 at a dose of 10 mg/kg. Blood samples (100 μL) for PK analysis were collected into EDTA microtainers (K$_2$ EDTA, the final concentration in blood sample is 0.25 mg/mL) from retro orbital plexus at pre-dose, 0.083, 0.25, 0.5, 1, 2, 4, 8, 24 hours post-dosing for PO and IV groups. Immediately after collection, blood collection tubes were gently inverted at least 5 times, ensuring complete mixing, then immediately placed on ice. The blood was centrifuged at 8000 rpm for 5 min at 4° C. to separate the plasma from the blood cells. After separation, 35 μL plasma was transferred into clean tube labeled by the compound name, animal number and timepoint. Plasma was stored at −80° C. until analysis.

Results are shown in Table 4, indicate the compound REX-P-7 has good bioavailability and good half-life.

The invention claimed is:

1. A five-membered heterocyclic amide Wnt pathway inhibitor having the following general structural formula, or a pharmaceutically acceptable salt thereof:

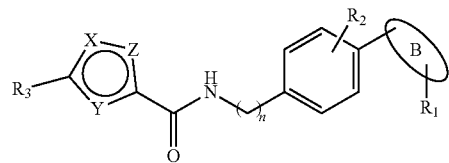

(2)

wherein

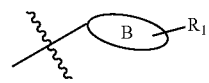

is selected from one of a group consisting of

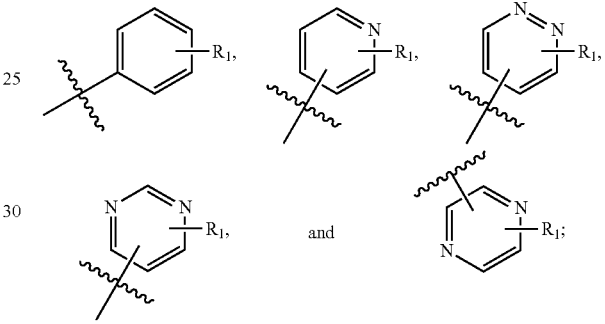

X, Y and Z are each independently selected from one of a group consisting of CR$_4$, NR$_5$, S atom and O atom, and the S atom and O atom are not present simultaneously;

n is selected from 1 or 2;

R$_1$ and R$_2$ is selected from one of a group consisting of hydrogen, halogen, C$_{1-6}$ alkyl, C$_{1-6}$ alkoxy, halogenated C$_{1-6}$ alkyl, halogenated C$_{1-6}$ alkoxy, amido, C$_{1-6}$ alkylamido, and heterocyclyl;

R$_3$ is selected from one of a group consisting of

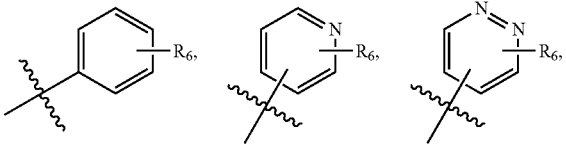

TABLE 4

Results of REX-P-7 Metabolic Stability and In Vivo PK

| | IV dose 5 mg/kg | | | | PO dose 10 mg/kg | | | | |
| --- | --- | --- | --- | --- | --- | --- | --- | --- | --- |
| | C$_{max}$/ Dose (ng/mL) | AUC0-t/ Dose (ng·h/mL) | CL (/F) (L/h/kg) | Vz/F (L/kg) | T$_{1/2}$ (h) | C$_{max}$/ Dose (ng/mL) | AUC0-t/ Dose (ng·h/mL) | T$_{1/2}$ (h) | F % | Eh % (HLM/ MLM) |
| REX-P-7 | 4167 | 5770 | 0.17 | 0.21 | 1.68 | 1923 | 2922 | 1.62 | 50.6 | 56.7/65 |

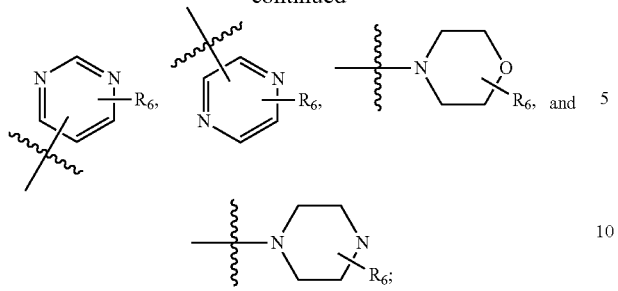

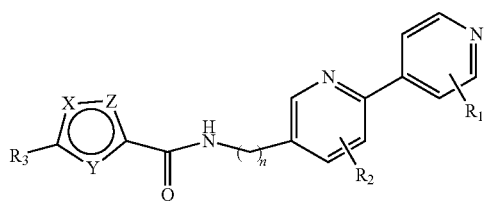

$R_4$ and $R_5$ are each independently selected from one of a group consisting of hydrogen, $C_{1-6}$ alkyl, halogenated $C_{1-6}$ alkyl, $C_{1-6}$ alkoxy, and halogenated $C_{1-6}$ alkoxy group, or $R_5$ is absent;

$R_6$ is selected from one of a group consisting of hydrogen, halogen, $C_{1-6}$ alkyl, halogenated $C_{1-6}$ alkyl, $C_{1-6}$ alkoxy, halogenated $C_{1-6}$ alkoxy, and amido group; and the heterocyclyl group is a 3-6 membered heterocyclic ring wherein the heterocyclyl group contains heteroatoms selected from N and O atoms.

2. The five-membered heterocyclic amide Wnt pathway inhibitor according to claim 1 having the following general structural formula, or a pharmaceutically acceptable salt thereof:

(3)

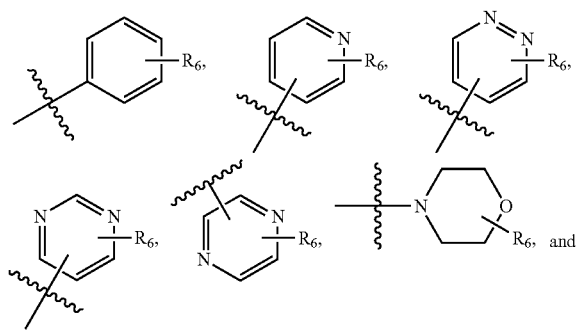

wherein X, Y and Z are each independently selected from one of a group consisting of $CR_4$, $NR_5$, S atom and O atom, and the S atom and O atom are not present simultaneously;

n is selected from 1 or 2;

$R_1$ and $R_2$ is selected from one of a group consisting of hydrogen, halogen, $C_{1-6}$ alkyl, $C_{1-6}$ alkoxy, halogenated $C_{1-6}$ alkyl, halogenated $C_{1-6}$ alkoxy, amido, $C_{1-6}$ alkylamido, and heterocyclyl;

$R_3$ is selected from one of a group consisting of

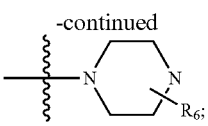

$R_4$ and $R_5$ are each independently selected from one of a group consisting of hydrogen, $C_{1-6}$ alkyl, halogenated $C_{1-6}$ alkyl, $C_{1-6}$ alkoxy, and halogenated $C_{1-6}$ alkoxy, or $R_5$ is absent;

$R_6$ is selected from one of a group consisting of hydrogen, halogen, $C_{1-6}$ alkyl, halogenated $C_{1-6}$ alkyl, $C_{1-6}$ alkoxy, halogenated $C_{1-6}$ alkoxy, and amido group; and the heterocyclyl group is a 3-6 membered heterocyclic ring wherein the heterocyclyl group contains heteroatoms selected from N and O atoms.

3. The five-membered heterocyclic amide Wnt pathway inhibitor according to claim 2 having the following general structural formula, or a pharmaceutically acceptable salt thereof:

(4)

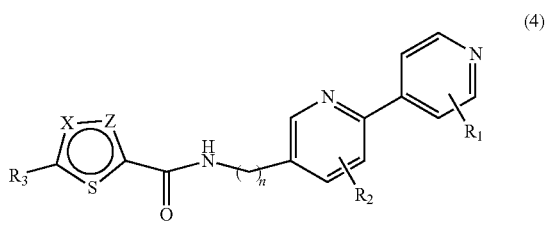

wherein X and Z are $CR_4$ at the same time; or X and Z are $NR_5$ at the same time; or any of X and Z is $CR_4$, and the other is $NR_5$;

n is selected from 1 or 2;

$R_1$ and $R_2$ is selected from one of a group consisting of hydrogen, halogen, $C_{1-6}$ alkyl, $C_{1-6}$ alkoxy, halogenated $C_{1-6}$ alkyl, halogenated $C_{1-6}$ alkoxy, amido, $C_{1-6}$ alkylamido, and heterocyclyl;

$R_3$ is selected from one of a group consisting of

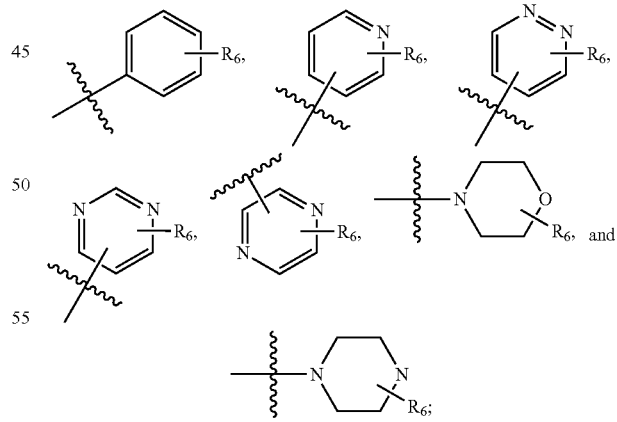

$R_6$ is selected from one of a group consisting of hydrogen, halogen, $C_{1-6}$ alkyl, halogenated $C_{1-6}$ alkyl, $C_{1-6}$ alkoxy, halogenated $C_{1-6}$ alkoxy, and amido group; and the heterocyclyl group is a 3-6 membered heterocyclic ring, wherein the heterocyclyl group contains heteroatoms selected from N and O atoms, wherein $R_5$ is absent.

4. The five-membered heterocyclic amide Wnt pathway inhibitor according to claim 2 having the following general structural formula, or a pharmaceutically acceptable salt thereof:

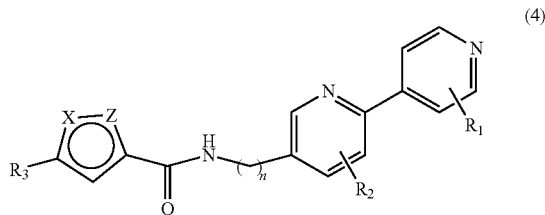

wherein X and Z are $CR_4$ at the same time; or X and Z are $NR_5$ at the same time; or any of X and Z is $CR_4$, and the other is $NR_5$; or any of X and Z is O atom, and the other is $NR_5$; or any of X and Z is O atom, and the other is $CR_4$;

n is selected from 1 or 2;

$R_1$ and $R_2$ is selected from one of a group consisting of hydrogen, halogen, $C_{1-6}$ alkyl, $C_{1-6}$ alkoxy, halogenated $C_{1-6}$ alkyl, halogenated $C_{1-6}$ alkoxy, amido, $C_{1-6}$ alkylamido, and heterocyclyl;

$R_3$ is selected from one of a group consisting of

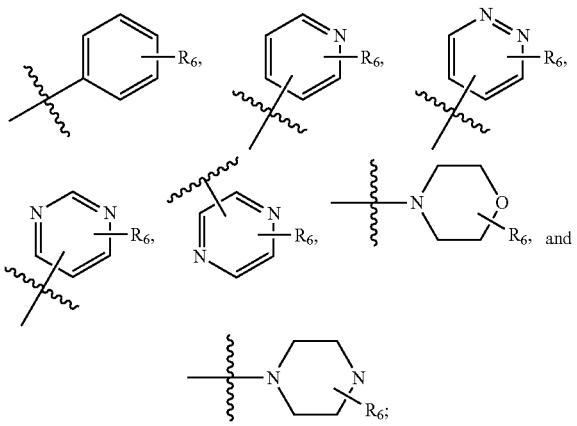

$R_6$ is selected from one of a group consisting of hydrogen, halogen, $C_{1-6}$ alkyl, halogenated $C_{1-6}$ alkyl, $C_{1-6}$ alkoxy, halogenated $C_{1-6}$ alkoxy, and amido group; and the heterocyclyl is a 3-6 membered heterocyclic ring containing one or more atom(s) selected from a group consisting of N and O atoms, wherein $R_5$ is absent.

5. A five-membered heterocyclic amide Wnt pathway inhibitor, selected from the following: N-((2',3-dimethyl-[2, 4'-bipyridin]-5-yl)methyl)-1-methyl-3-phenyl-1H-pyrazole-5-carboxamide;

N-((2',3-dimethyl[2,4'-bipyridin]-5-yl)methyl)-5-phenyl-1H-pyrazole-3-carboxamide;
N-((2',3-dimethyl[2,4'-bipyridin]-5-yl)methyl)-2-phenylthiazole-5-carboxamide;
N-((2',3-dimethyl[2,4'-bipyridin]-5-yl)methyl)-5-phenylthiazole-2-carboxamide;
N-((2',3-dimethyl[2,4'-bipyridin]-5-yl)methyl)-2-phenylthiazole-4-carboxamide;
N-((2',3-dimethyl[2,4'-bipyridin]-5-yl)methyl)-4-phenylthiazole-2-carboxamide;
N-((2',3-dimethyl[2,4'-bipyridin]-5-yl)methyl)-5-phenylisoxazole-3-carboxamide;
N-((2',3-dimethyl-[2,4'-bipyridin]-5-yl)methyl)-5-phenyl-1,3,4-thiadiazole-2-carboxamide;
N-((2',3-dimethyl-[2,4'-bipyridin]-5-yl)methyl)-1-methyl-5-phenyl-1H-pyrazole-3-carboxamide;
N-((2',3-dimethyl-[2,4'-bipyridin]-5-yl)methyl)-4-methyl-5-phenylthiazole-2-carboxamide;
5-(2-chlorophenyl)-N-((2',3-dimethyl-[2,4'-bipyridin]-5-yl)methyl)thiazole-2-carboxamide;
5-(3-chlorophenyl)-N-((2',3-dimethyl-[2,4'-bipyridin]-5-yl)methyl)thiazole-2-carboxamide;
5-(4-chlorophenyl)-N-((2',3-dimethyl-[2,4'-bipyridin]-5-yl)methyl)thiazole-2-carboxamide;
N-((2',3-dimethyl-[2,4'-bipyridin]-5-yl)methyl)-5-(pyridin-2-yl)thiazole-2-carboxamide;
N-((2',3-dimethyl-[2,4'-bipyridin]-5-yl)methyl)-5-(pyrazin-2-yl)thiazole-2-carboxamide;
N-((2',3-dimethyl-[2,4'-bipyridin]-5-yl)methyl)-5-(pyridin-2-yl)-1H-pyrazole-3-carboxamide;
N-((2',3-dimethyl-[2,4'-bipyridin]-5-yl)methyl)-5-(3-fluoropyridin-2-yl)-1H-pyrazole-3-carboxamide;
N-((2',3-dimethyl-[2,4'-bipyridin]-5-yl)methyl)-5-(5-fluoropyridin-3-yl)-1H-pyrazole-3-carboxamide;
N-((2',3-dimethyl-[2,4'-bipyridin]-5-yl)methyl)-5-(6-methylpyridin-2-yl)-1H-pyrazole-3-carboxamide;
N-((2',3-dimethyl-[2,4'-bipyridin]-5-yl)methyl)-5-(pyrimidin-2-yl)-1H-pyrazole-3-carboxamide;
N-((2',3-dimethyl-[2,4'-bipyridin]-5-yl)methyl)-5-(pyrazin-2-yl)-1H-pyrazole-3-carboxamide;
N-((2',3-dimethyl-[2,4'-bipyridin]-5-yl)methyl)-5-(pyrazin-2-yl)-1H-pyrazole-3-carboxamide;
N-((2',3-dimethyl-[2,4'-bipyridin]-5-yl)methyl)-2-(pyridin-2-yl)thiazole-5-carboxamide;
N-((2',3-dimethyl-[2,4'-bipyridin]-5-yl)methyl)-2-(3-fluoropyridin-2-yl)thiazole-5-carboxamide;
N-((2',3-dimethyl-[2,4'-bipyridin]-5-yl)methyl)-2-(5-fluoropyridin-3-yl)thiazole-5-carboxamide;
N-((2',3-dimethyl-[2,4'-bipyridin]-5-yl)methyl)-2-(6-methylpyridin-2-yl)thiazole-5-carboxamide;
N-((2',3-dimethyl-[2,4'-bipyridin]-5-yl)methyl)-2-(pyrimidin-2-yl)thiazole-5-carboxamide;
N-((2',3-dimethyl-[2,4'-bipyridin]-5-yl)methyl)-2-(pyrazin-2-yl)thiazole-5-carboxamide;
N-((2',3-dimethyl[2,4'-bipyridin]-5-yl)methyl)-5-(pyridin-2-yl)isoxazole-3-carboxamide;
N-((2',3-dimethyl[2,4'-bipyridin]-5-yl)methyl)-5-(3-fluoropyridin-2-yl)isoxazole-3-carboxamide;
N-((2',3-dimethyl[2,4'-bipyridin]-5-yl)methyl)-5-(5-fluoropyridin-3-yl)isoxazole-3-carboxamide;
N-((2',3-dimethyl[2,4'-bipyridin]-5-yl)methyl)-5-(6-methylpyridin-2-yl)isoxazole-3-carboxamide;
N-((2',3-dimethyl-[2,4'-bipyridin]-5-yl)methyl)-5-(pyrimidin-2-yl)isoxazole-3-carboxamide;
N-((2',3-dimethyl[2,4'-bipyridin]-5-yl)methyl)-5-(pyrazin-2-yl)isoxazole-3-carboxamide;
5-(4-acetylpiperazin-1-yl)-N-((2',3-dimethyl-[2,4'-bipyridin]-5-yl)methyl)isoxazole-3-carboxamide;
N-((2',3-dimethyl-[2,4'-bipyridin]-5-yl)methyl)-5-(pyridin-3-yl)thiazole-2-carboxamide;
N-((2',3-dimethyl-[2,4'-bipyridin]-5-yl)methyl)-5-(3-fluoropyridin-2-yl)thiazole-2-carboxamide;
N-((2',3-dimethyl-[2,4'-bipyridin]-5-yl)methyl)-5-(5-fluoropyridin-3-yl)thiazole-2-carboxamide;
N-((2',3-dimethyl-[2,4'-bipyridin]-5-yl)methyl)-5-(6-methylpyridin-2-yl)thiazole-2-carboxamide;

N-((2',3-dimethyl-[2,4'-bipyridin]-5-yl)methyl)-5-(pyrimidin-2-yl)thiazole-2-carboxamide;
N-((2',3-dimethyl-[2,4'-bipyridin]-5-yl)methyl)-5-(pyrimidin-5-yl)thiazole-2-carboxamide;
5-(4-acetylpiperazin-1-yl)-N-((2',3-dimethyl-[2,4'-bipyridin]-5-yl)methyl)-1,3,4-thiadiazole-2-carboxamide;
5-(4-acetylpiperazin-1-yl)-N-((2',3-dimethyl-[2,4'-bipyridin]-5-yl)methyl)thiazole-2-carboxamide;
2-(4-acetylpiperazin-1-yl)-N-((2',3-dimethyl-[2,4'-bipyridin]-5-yl)methyl)thiazole-5-carboxamide;
5-(3-chlorophenyl)-N-((2',3-dimethyl-[2,4'-bipyridin]-5-yl)methyl)-1,3,4-thiadiazole-2-carboxamide;
N-((2',3-dimethyl-[2,4'-bipyridin]-5-yl)methyl)-5-(3-fluorophenyl)-1,3,4-thiadiazole-2-carboxamide;
N-((2',3-dimethyl-[2,4'-bipyridin]-5-yl)methyl)-5-(pyridin-2-yl)-1,3,4-thiadiazole-2-carboxamide;
N-((2',3-dimethyl-[2,4'-bipyridin]-5-yl)methyl)-5-(3-fluoropyridin-2-yl)-1,3,4-thiadiazole-2-carboxamide;
N-((2',3-dimethyl-[2,4'-bipyridin]-5-yl)methyl)-5-(5-fluoropyridin-3-yl)-1,3,4-thiadiazole-2-carboxamide;
N-((2',3-dimethyl-[2,4'-bipyridin]-5-yl)methyl)-5-(6-methylpyridin-2-yl)-1,3,4-thiadiazole-2-carboxamide;
N-((2',3-dimethyl-[2,4'-bipyridin]-5-yl)methyl)-5-(pyrimidin-2-yl)-1,3,4-thiadiazole-2-carboxamide;
N-((2',3-dimethyl-[2,4'-bipyridin]-5-yl)methyl)-5-(pyrazin-2-yl)-1,3,4-thiadiazole-2-carboxamide;
N-((2',3-dimethyl-[2,4'-bipyridin]-5-yl)methyl)-5-(5-methylpyridin-3-yl)-1,3,4-thiadiazole-2-carboxamide;
N-((2',3-dimethyl-[2,4'-bipyridin]-5-yl)methyl)-5-(2-methylpyridin-3-yl)-1,3,4-thiadiazole-2-carboxamide;
N-((2',3-dimethyl-[2,4'-bipyridin]-5-yl)methyl)-5-(4-methylpyridin-3-yl)-1,3,4-thiadiazole-2-carboxamide; and
N-((2',3-dimethyl-[2,4'-bipyridin]-5-yl)methyl)-5-(3-methylpyridin-2-yl)-1,3,4-thiadiazole-2-carboxamide.

6. A pharmaceutical composition, comprising the compound or a pharmaceutically acceptable salt thereof as defined in claim 1 and one or more pharmaceutically acceptable carriers.

7. A method of antagonizing a Wnt signalling pathway, comprising administering to a subject an effective amount of the compound or a pharmaceutically acceptable salt thereof as defined in claim 1.

8. The five-membered heterocyclic amide Wnt pathway inhibitor according to claim 1, wherein the halogen is selected from the group consisting of fluorine and chlorine.

9. The five-membered heterocyclic amide Wnt pathway inhibitor according to claim 2, wherein the halogen is selected from the group consisting of fluorine and chlorine.

* * * * *